United States Patent
Li et al.

(10) Patent No.: US 12,336,794 B2
(45) Date of Patent: Jun. 24, 2025

(54) SPHYGMOMANOMETER

(71) Applicant: OMRON HEALTHCARE CO., LTD., Muko (JP)

(72) Inventors: Zhe Li, Kyoto (JP); Toshihiko Ogura, Kyoto (JP); Toshiaki Koga, Kyoto (JP); Akira Oshiumi, Kyoto (JP); Yoshihide Tokko, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 819 days.

(21) Appl. No.: 17/479,625

(22) Filed: Sep. 20, 2021

(65) Prior Publication Data

US 2022/0000380 A1    Jan. 6, 2022

Related U.S. Application Data

(63) Continuation of application No. PCT/JP2020/011776, filed on Mar. 17, 2020.

(30) Foreign Application Priority Data

Apr. 3, 2019   (JP) .................... 2019-071535

(51) Int. Cl.
*A61B 5/022*    (2006.01)
*A61B 5/00*    (2006.01)
(Continued)

(52) U.S. Cl.
CPC ...... *A61B 5/02225* (2013.01); *A61B 5/02141* (2013.01); *A61B 5/0235* (2013.01); *A61B 5/742* (2013.01); *A61B 2562/0247* (2013.01)

(58) Field of Classification Search
None
See application file for complete search history.

(56) References Cited

U.S. PATENT DOCUMENTS

2008/0319329 A1* 12/2008 Tseng ................ A61B 5/0235
                                                                 600/490
2010/0331709 A1* 12/2010 Matsumura ........ A61B 5/02422
                                                                 600/490
(Continued)

FOREIGN PATENT DOCUMENTS

CN    205458888 U    8/2016
JP    2002-078686 A    3/2002
(Continued)

OTHER PUBLICATIONS

Jun. 2, 2020 Search Report issued in International Patent Application No. PCT/JP2020/011776.

*Primary Examiner* — Aurelie H Tu
(74) *Attorney, Agent, or Firm* — Oliff PLC

(57) ABSTRACT

A sphygmomanometer according to the present invention includes an air leakage testing unit that performs air leakage testing on an air system to obtain an air leakage testing result, and a storage unit that stores the air leakage testing result. The air leakage testing result stored in the storage unit is displayed, on a display device, in a first display mode during a transition from a power-off state to a standby state or a non-blood pressure measurement state where a measurement start operation is disabled, or during a transition from the standby state to the power off state or the non-blood pressure measurement state where the measurement start operation is disabled, whereas, in the standby state or during blood pressure measurement, the air leakage testing result is not displayed or is displayed in a second display mode lower in degree of enhancement than the first display mode.

6 Claims, 19 Drawing Sheets

(51) Int. Cl.
*A61B 5/021* (2006.01)
*A61B 5/0235* (2006.01)

(56) References Cited

U.S. PATENT DOCUMENTS

| | | | | |
|---|---|---|---|---|
| 2011/0282221 A1* | 11/2011 | Sawanoi | ............ | A61B 5/02141 |
| | | | | 600/493 |
| 2019/0104950 A1* | 4/2019 | Mori | ................. | A61B 5/02225 |
| 2019/0365245 A1* | 12/2019 | Tsutsumi | ........... | A61B 5/02233 |

FOREIGN PATENT DOCUMENTS

| | | |
|---|---|---|
| JP | 2007-007038 A | 1/2007 |
| JP | 2010-178908 A | 8/2010 |
| WO | 2009/093515 A1 | 7/2009 |
| WO | 2010/067752 A1 | 6/2010 |
| WO | 2010/090072 A1 | 8/2010 |

\* cited by examiner

AIR LEAKAGE LEVEL L2
FIRST DISPLAY MODE

THE ARM CUFF NEEDS TO BE REPLACED WITH A NEW ARM CUFF IN ORDER TO MAKE CORRECT MEASUREMENT.

NOTIFICATION ABOUT ARM CUFF REPLACEMENT

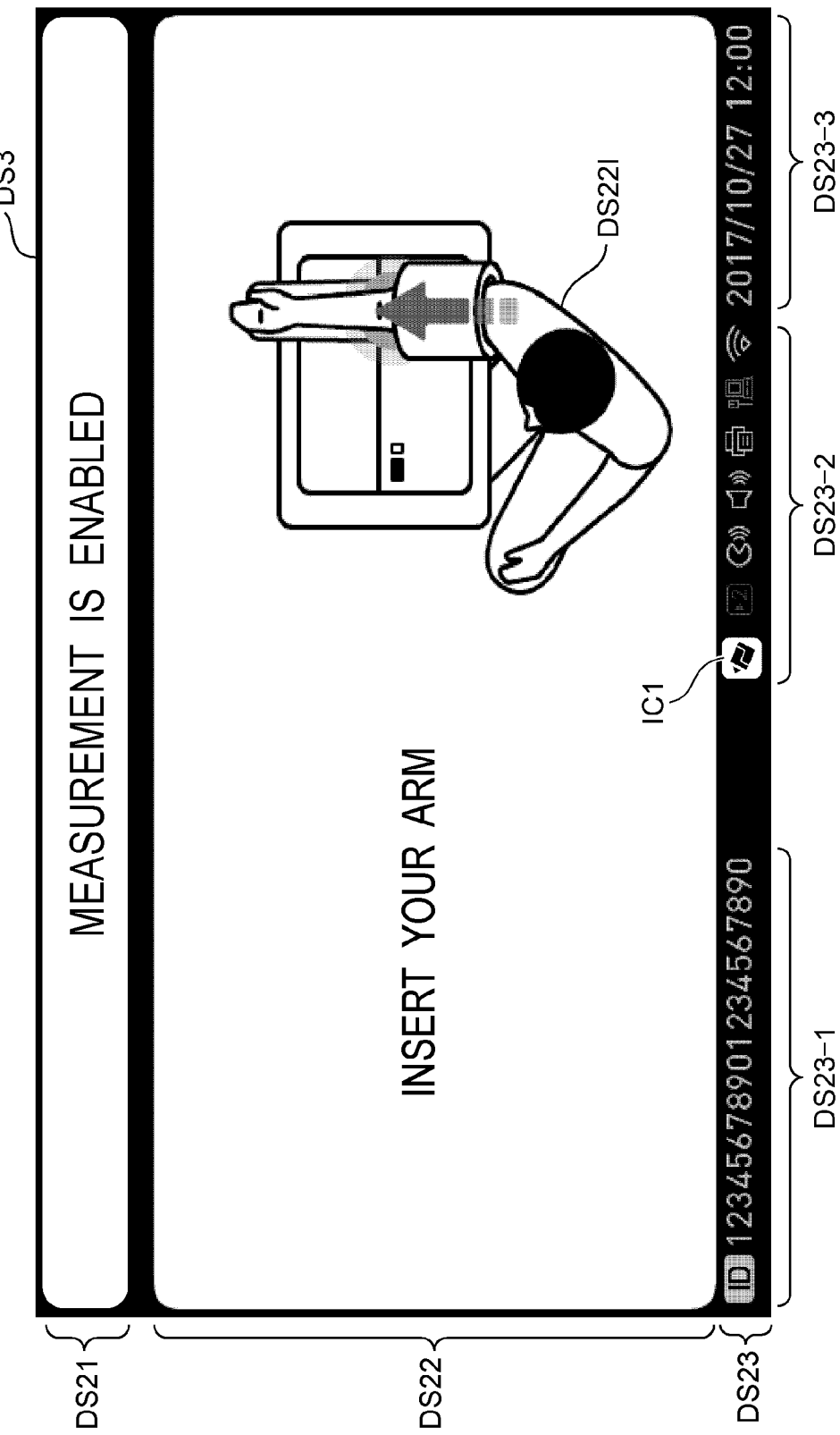

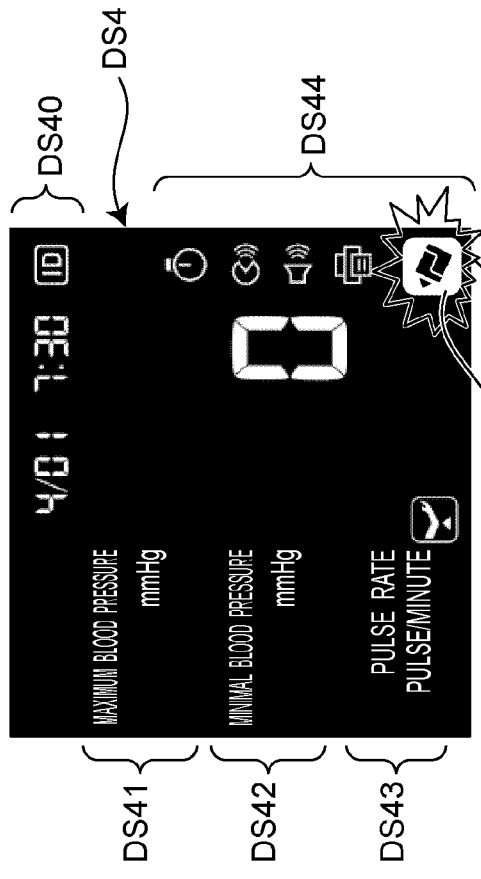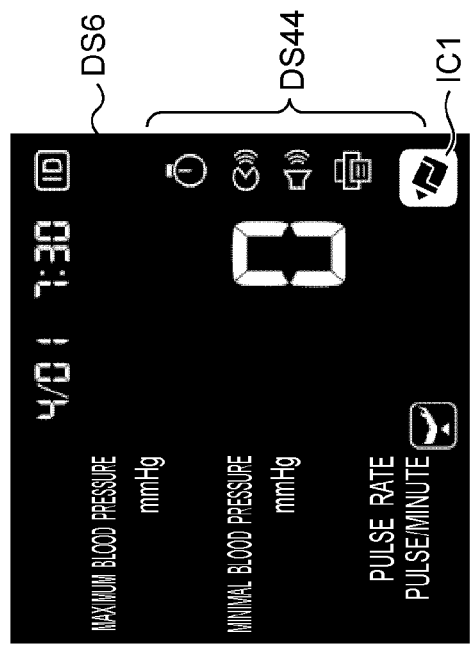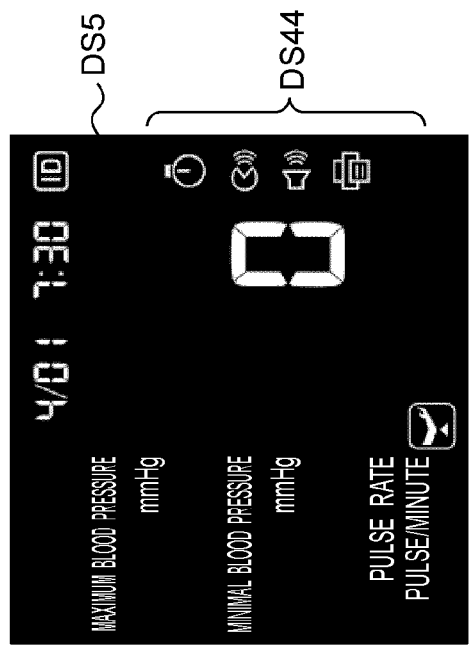
Fig. 17A  AIR LEAKAGE LEVEL L2
FIRST DISPLAY MODE
Fig. 17B  AIR LEAKAGE LEVEL L2
EXAMPLE WHERE AIR LEAKAGE TESTING RESULT IS NOT DISPLAYED
Fig. 17C  AIR LEAKAGE LEVEL L2
SECOND DISPLAY MODE

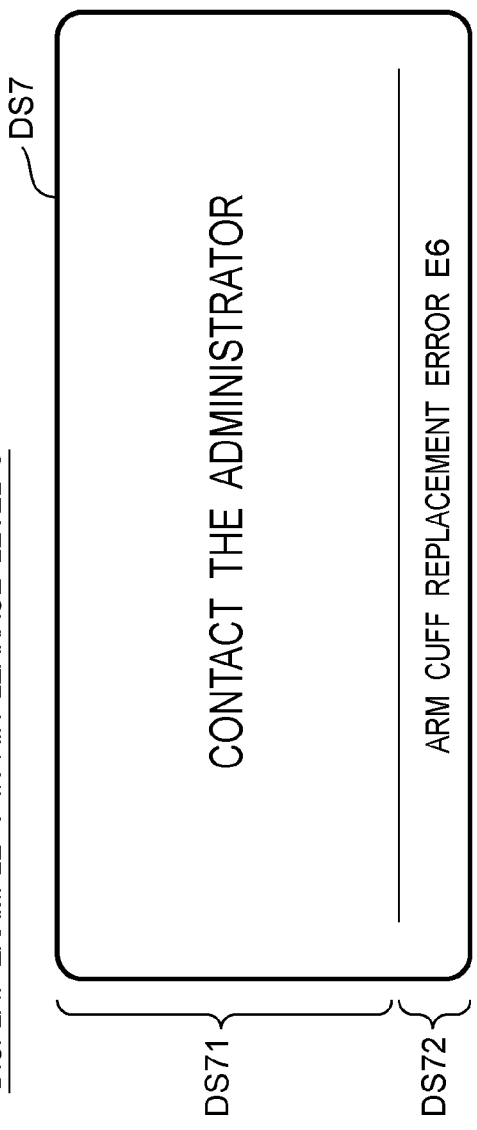
Fig.18A   DISPLAY EXAMPLE 1 IN AIR LEAKAGE LEVEL 3
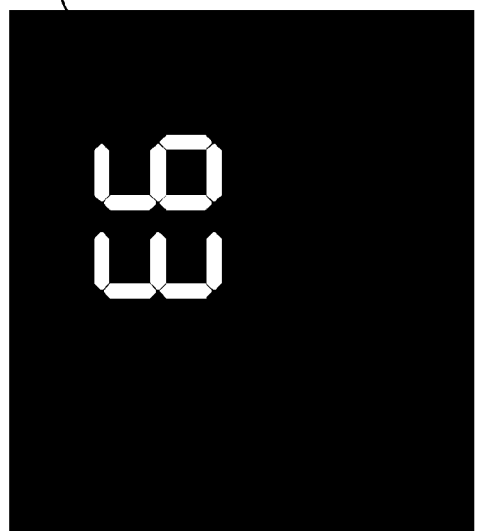
Fig.18B   DISPLAY EXAMPLE 2 IN AIR LEAKAGE LEVEL 3

SPHYGMOMANOMETER

CROSS-REFERENCE TO RELATED APPLICATION

This application is based on an application No. 2019-071535 filed in Japan on Apr. 3, 2019, the entire content of which is hereby incorporated by reference.

TECHNICAL FIELD

The present invention relates to a sphygmomanometer, and more particularly to a sphygmomanometer provided with an air system for use in blood pressure measurement and capable of performing air leakage testing on the air system.

BACKGROUND ART

In the related art, as this type of sphygmomanometer, a sphygmomanometer that includes an air system (an air bag, an air pipe, and the like) for use in blood pressure measurement and performs air leakage testing on the air system to detect a presence of air leakage is known, as disclosed in Patent Literature 1 (JP 2010-178908 A), for example. In the above-described sphygmomanometer, when it is determined that there is air leakage, a testing result indicating that there is abnormal air leakage is displayed on a display device. This allows a user of the sphygmomanometer to take a measure such as contacting a service center or the like of a manufacturer to request a repair for the sphygmomanometer.

SUMMARY OF INVENTION

In a case where the sphygmomanometer is used in an ordinary household, when it is determined that there is air leakage, it is sufficient that the testing result indicating that there is abnormal air leakage is simply provided on the display device. On the other hand, in a case where the sphygmomanometer is used in a medical institution such as a hospital, when general patients notice the air leakage testing result, many of the patients variously inform personnel of the medical institution (receptionist, maintenance personnel (medical engineer), doctor, nurse, or the like) that there is abnormal air leakage. This causes inconveniences in operation of equipment management in the medical institution. Further, since the air leakage gradually increases, it is not necessary to notify the general patients because there is no problem in blood pressure measurement at an initial stage of the air leakage, but it is necessary to notify the personnel of the medical institution of a necessity of maintenance as early as possible.

It is therefore an object of the present invention to provide a sphygmomanometer provided with an air system for use in blood pressure measurement and capable of performing air leakage testing on the air system, wherein an air leakage testing result can be notified to personnel of a medical institution in a mode difficult for a general patient to understand.

In order to achieve the above object, a sphygmomanometer according to the present disclosure is a sphygmomanometer provided with an air system for use in blood pressure measurement and capable of performing air leakage testing on the air system, the sphygmomanometer comprising:

a main control unit configured to perform main control to make a transition from a power-off state to a standby state in response to a power-on operation, to perform blood pressure measurement using the air system in response to a measurement start operation in the standby state and make a transition to the standby state after the blood pressure measurement, and to make a transition to the power-off state in response to a power-off operation in the standby state;

an air leakage testing unit configured to perform air leakage testing on the air system to obtain an air leakage testing result of the air leakage testing;

a storage unit configured to store the air leakage testing result; and a notification control unit configured to perform notification control to make displaying, on a display device, the air leakage testing result stored in the storage unit in a first display mode during the transition from the power-off state to the standby state or a transition from the power-off state to a non-blood pressure measurement state where the measurement start operation is disabled, or during the transition from the standby state to the power-off state or a transition from the standby state to the non-blood pressure measurement state where the measurement start operation is disabled, and not to make displaying the air leakage testing result or to make displaying the air leakage testing result in a second display mode lower in degree of enhancement than the first display mode in the standby state or during the blood pressure measurement.

Herein, a "power-off state" refers to a state where power is not supplied to the sphygmomanometer.

A "power-on operation" refers to an operation of powering on the sphygmomanometer by, for example, personnel of a medical institution such as an operation of switching on a power switch provided on the sphygmomanometer or an operation of connecting a power cable connected to the sphygmomanometer to a power outlet. Conversely, a "power-off operation" refers to an operation of powering off the sphygmomanometer by, for example, the personnel of the medical institution such as operation of switching off the power switch provided on the sphygmomanometer or an operation of removing the power cable connected to the sphygmomanometer from a power outlet. The "power-on operation" and the "power-off operation" may be each, for example, a remote operation using radio communication.

A "measurement start operation" refers to an operation of pressing a measurement start switch provided on the sphygmomanometer by, for example, a subject (typically, a patient). Further, for example, when the sphygmomanometer includes a tubular cuff and a sensor that detects insertion of an arm into the cuff and is configured to start to perform blood pressure measurement in accordance with an output of the sensor (indicating that the arm is inserted into the cuff), the "measurement start operation" may correspond to an operation of inserting his/her arm into the cuff by the subject.

A "standby state" refers to a state of waiting for the measurement start operation, that is, a state of being ready to perform blood pressure measurement in response to the measurement start operation. The standby state allows a display device to provide a display (for example, a display indicating that power is being supplied). With the sphygmomanometer installed in a medical institution such as a hospital, a general patient usually would see the sphygmomanometer only when the sphygmomanometer is in the standby state or is in operation for the blood pressure measurement.

A "non-blood pressure measurement state where the measurement start operation is disabled" refers to a non-blood pressure measurement state similar to the standby state but different from the standby state in that the measurement start operation is disabled. Examples of the "non-blood pressure measurement state where the measurement start operation is disabled" include a state where the sphygmomanometer is under maintenance (maintenance mode), and a state where various settings that define the operation of the sphygmomanometer are made (setting mode).

A "first display mode" for the displaying the air leakage testing result is defined as a mode where, for example, a person viewing the display can easily recognize the air leakage testing result. A "second display mode" is a mode lower in degree of enhancement than the first display mode, that is, an inconspicuous mode.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 16 is a diagram illustrating a display example where, when the air leakage testing result is the second air leakage level, the air leakage testing result is displayed in a second display mode lower in degree of enhancement than the first display mode (FIG. 14).

FIG. 17A is a diagram illustrating a display example in the first display mode where, when the air leakage testing result is the second air leakage level, an icon corresponding to the air leakage testing result is caused to blink.

FIG. 17B is a diagram illustrating an example where, when the air leakage testing result is the second air leakage level, the air leakage testing result is not displayed.

FIG. 17C is a diagram illustrating a display example where, when the air leakage testing result is the second air leakage level, the air leakage testing result is displayed in the second display mode lower in degree of enhancement than the first display mode (FIG. 17A).

FIG. 18A is a diagram illustrating an example (display example 1) where, when the air leakage testing result is a third air leakage level, the air leakage testing result is displayed in a dot matrix mode.

FIG. 18B is a diagram illustrating another example (display example 2) where, when the air leakage testing result is the third air leakage level, the air leakage testing result is displayed in a segment mode.

DESCRIPTION OF EMBODIMENTS

An embodiment of the present invention will be described in detail below with reference to the drawings.

Schematic Configuration of Main Body

Figure 1:
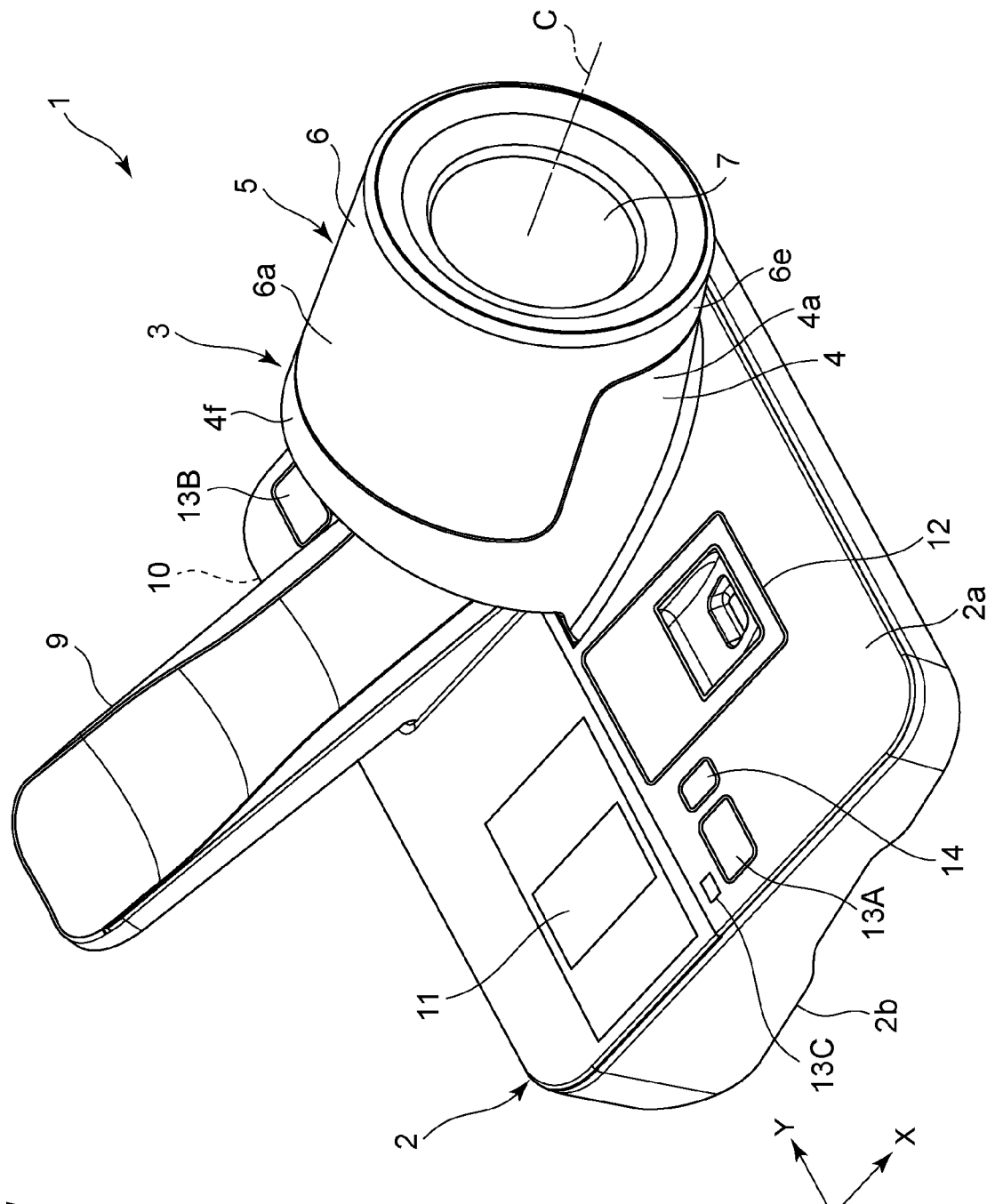
FIG. 1 is a diagram illustrating a sphygmomanometer including a main body and a cuff unit according to an embodiment of the present invention as viewed from a diagonally forward and upward position.

FIG. 1 illustrates a sphygmomanometer (denoted by a reference numeral 1) according to the embodiment of the present invention as viewed from a diagonally forward and upward position. Note that, in FIG. 1, an XYZ orthogonal coordinate system is also illustrated for the sake of clarity. The X axis extends in a front-rear direction, the Y axis extends in a left-right direction, and the Z axis extends in an up-down direction. As illustrated in FIG. 1, the sphygmomanometer 1 primarily includes a main body 2, a cuff 3, and an armrest 9. The sphygmomanometer 1 is designed for medical professional use and is assumed to be installed in a hospital serving as a medical institution in this example. The sphygmomanometer 1 is designed to measure blood pressure at an upper arm as a to-be-measured part of a subject (typically, a patient) in response to an operation made by the subject him/herself.

The cuff 3 having an approximately cylindrical shape is disposed on a right front portion of an upper surface 2a of the main body 2. In this example, a center axis C of the cuff 3 is inclined in such a manner that a height gradually decreases (Z coordinate decreases) from the front toward the rear (in the -X direction). A bottom surface 2b of the main body 2 has an approximately flat shape and is placed on a horizontal plane (a table-like surface along the XY plane) (not illustrated).

The armrest 9 is disposed on a right rear portion of the upper surface 2a of the main body 2. The armrest 9 has an approximately arc-shaped cross section opened upward, and approximately linearly extends rearward of the main body 2 from an opening on a rear side of the cuff 3 at an inclination steeper than an inclination of the upper surface 2a of the main body 2. For blood pressure measurement, the subject sits in front of the main body 2 and inserts his/her arm from a front side (side facing the subject) of the cuff 3 to the rear side of the cuff 3, so that the upper arm of the subject is located in the cuff 3, and the forearm is placed on the armrest 9.

On a left front portion of the upper surface 2a of the main body 2, a measurement start/stop switch 13A for the subject to operate to start or stop measurement with his/her left hand, a mode switch 13C for selecting a function of the sphygmomanometer 1, a measurement result displaying-stop switch 14 for a user to operate to stop displaying a blood pressure measurement result, and a printer 12 for instructing to print out the blood pressure measurement result are arranged. On a left rear portion of the upper surface 2a of the main body 2, a display device (in this example, a liquid crystal display (LCD)) 11 to be used to display the blood pressure measurement result is disposed. Note that the display device 11 may be installed in a standing manner on the upper surface 2a of the main body 2 to cause its display screen to face the subject. Further, adjacent to a right side of the armrest 9 on the upper surface 2a of the main body 2, a measurement start/stop switch 13B for the user to operate to start or stop measurement with his/her right hand is disposed. The measurement start/stop switches 13A, 13B and the measurement result displaying-stop switch 14 are each designed to temporarily operate (input an instruction) only when pressed. Note that the two measurement start/stop switches 13A, 13B are respectively provided to help the subject to proceed measurement in a condition where his/her right upper arm or left upper arm is inserted through the cuff 3. In the following example, for the sake of simplicity, it is assumed that only the measurement start/stop switch 13A is used out of the two measurement start/stop switches 13A, 13B.

Further, a rear surface (-X side surface) of the main body 2 is provided with a power supply connector (not illustrated) to which a commercial power supply (in this example, AC 100 V) is supplied, and a power switch 10 to be used to turn on and off power supply from the commercial power supply. When turned on (power-on operation), the power switch 10 maintains a state (power-on state) where power from the commercial power source is supplied, and when turned off (power-off operation), the power switch 10 maintains a state (power-off state) where power supply from the commercial power source is interrupted.

The cuff 3 includes a slide receiver 4 provided on the main body 2 and a cuff unit 5 that has a cylindrical shape and is detachably attached to the slide receiver 4.

The slide receiver 4 includes, in an integral manner, a front side portion 4a having an arc-shaped (semicircular in this example) cross section opened upward, and a rear side portion 4f extending from the rear of the front side portion 4a and having a circular cross section concentric with the arc-shaped cross section of the front side portion 4a (center axis C).

The cuff unit 5 includes a cuff frame 7 having a cylindrical shape for an upper arm 90 to be inserted, and a cover 6 detachably attached to the cuff frame 7 to cover the cuff frame 7.

The cover 6 includes, in an integral manner, a rear side portion 6a having an arc-shaped (semicircular in this example) cross section opened downward, and a front side portion 6e extending from the front of the rear side portion 6a and having a circular cross section concentric with the arc-shaped cross section of the rear side portion 6a (center axis C).

Figure 2A:
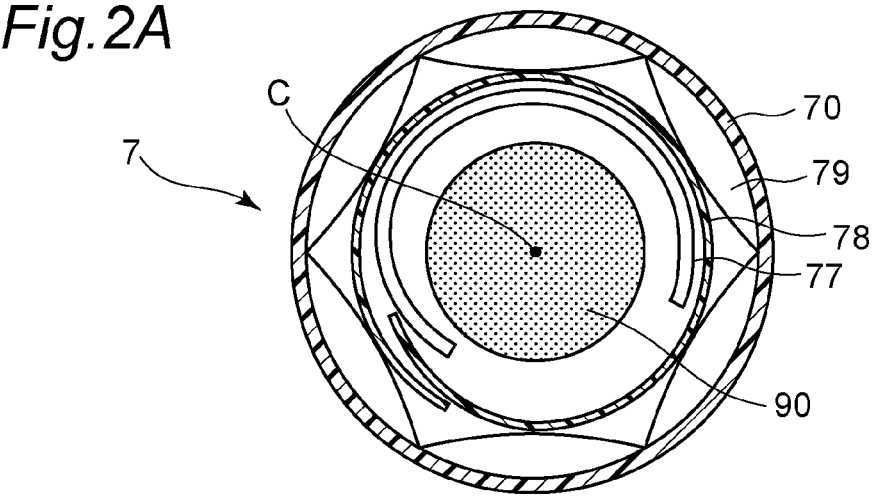
FIGS. 2A to 2C are diagrams illustrating how the cuff unit operates during blood pressure measurement.

As illustrated in FIG. 2A (illustrating a cross section perpendicular to the center axis C of the cuff unit 5), the cuff frame 7 includes an outer peripheral member 70 having a cylindrical shape, a winding cuff 79 serving as a winding air bag annularly disposed along an inner circumferential surface of the outer peripheral member 70, a curler 78 formed of a flexible plate material curved and disposed along an inner circumferential surface of the winding cuff 79, and a measurement cuff 77 serving as a measurement air bag disposed along an inner circumferential surface of the curler 78, the measurement cuff 77 being pressurized for the blood pressure measurement to compress the upper arm 90.

The winding cuff 79 is made of a stretchable resin (for example, polyurethane), and, in this example, is divided into six portions along the inner circumferential surface of the outer peripheral member 70.

The curler 78 is made of a resin (for example, polypropylene) having suitable flexibility and is produced to have a flat plate shape in an unfolded state, but have an approximately annular shape surrounding the upper arm 90 in the state illustrated in FIG. 2A (natural state), and have its ends in a circumferential direction overlapping each other.

Like the winding cuff 79, the measurement cuff 77 is made of a stretchable resin (for example, polyurethane). The measurement cuff 77 has a length (circumferential dimension) enough to surround about two thirds or more of the upper arm 90 along the inner circumferential surface of the curler 78 (note that, in the state illustrated in FIG. 2A, the circumferential ends of the measurement cuff 77 relatively largely separate from each other).

Block Configuration of Air System and Control System

Figure 3:
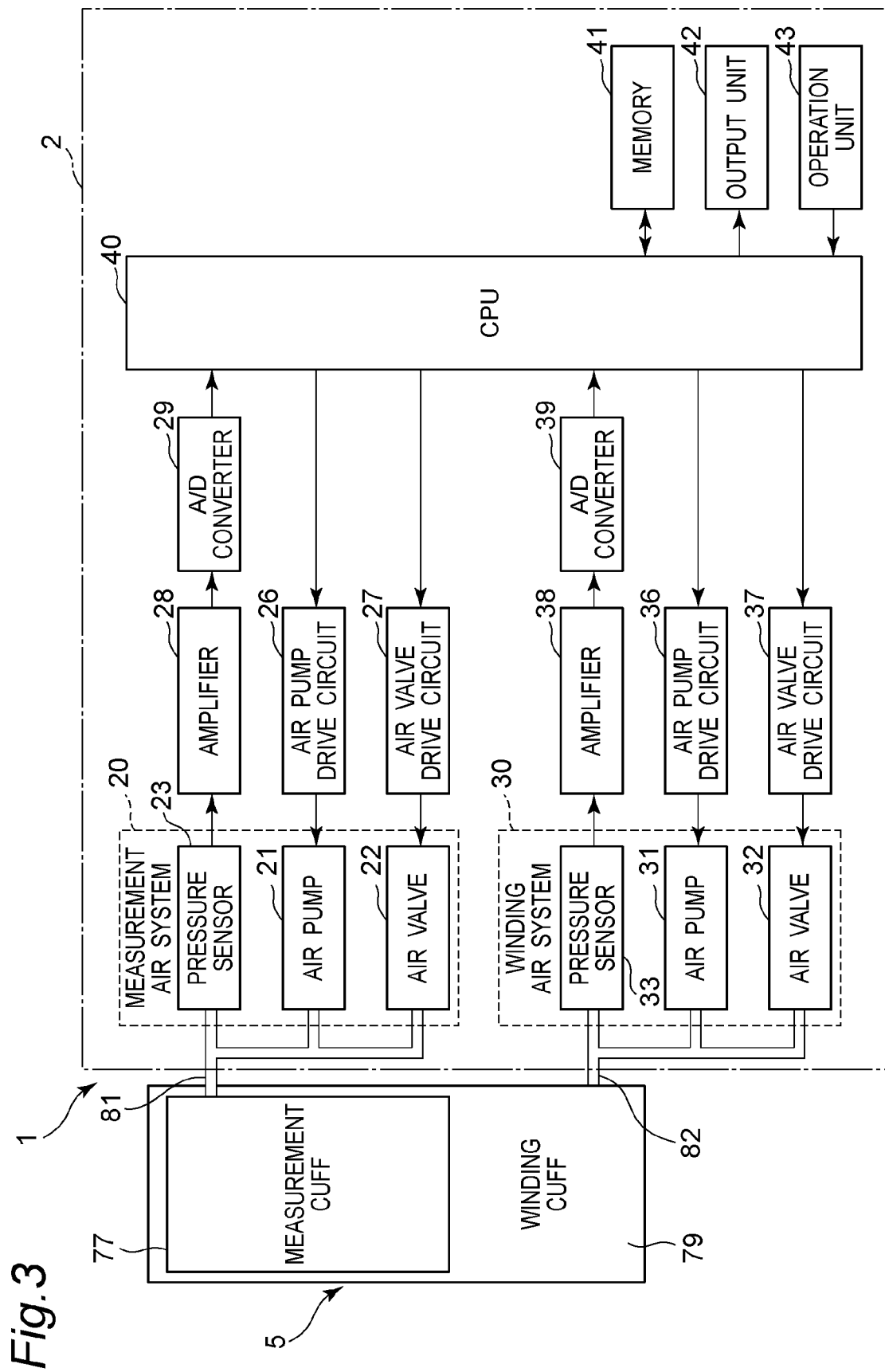
FIG. 3 is a diagram illustrating a block configuration including an air system and a control system in the sphygmomanometer with the cuff unit attached to the main body.

FIG. 3 illustrates a block configuration including an air system and control system of the sphygmomanometer 1 with the cuff unit 5 attached to the main body 2. As illustrated in FIG. 3, the measurement cuff 77 in the cuff unit 5 is connected to a measurement air system 20 in the main body 2 via a fluid pipe 81. The winding cuff 79 in the cuff unit 5 is connected to a winding air system 30 in the main body 2 via a fluid pipe 82. Further, the measurement air system 20 and the winding air system 30 operate under control of a central processing unit (CPU) 40.

The measurement air system 20 includes an air pump 21, an air valve 22, and a pressure sensor 23 in addition to the measurement cuff 77. The air pump 21 is configured to pressurize the inside of the measurement cuff 77 and is driven by an air pump drive circuit 26 in accordance with an instruction from the CPU 40. The air pump 21 feeds air as a fluid to make the pressure in the measurement cuff 77 reach a predetermined pressure during the blood pressure measurement.

The air valve 22 is configured to maintain or reduce the pressure in the measurement cuff 77 and opens or closes under control of an air valve drive circuit 27 in accordance with an instruction from the CPU 40. The air valve 22 maintains or reduces the pressure in the measurement cuff 77 that has become high by the air pump 21 during the blood pressure measurement, and after completion of a blood pressure calculation, rapidly exhausts air from the inside of the measurement cuff 77 to return the inside of the measurement cuff 77 to atmospheric pressure.

The pressure sensor 23 is configured to detect the pressure in the measurement cuff 77, and detects the pressure in the measurement cuff 77 that varies with time from the start of the blood pressure measurement to the completion of the blood pressure calculation and outputs a signal corresponding to the detected value to an amplifier 28. The amplifier 28 amplifies the signal output from the pressure sensor 23 and outputs the signal thus amplified to an A/D converter 29. The A/D converter 29 converts the analog signal output from the amplifier 28 to digital form and outputs the digital signal to the CPU 40.

The winding air system 30 includes an air pump 31, an air valve 32, and a pressure sensor 33 in addition to the winding cuff 79. The air pump 31 is configured to pressurize the inside of the winding cuff 79 and is driven by an air pump drive circuit 36 in accordance with an instruction from the CPU 40. The air pump 31 feeds air as a fluid to make the pressure in the winding cuff 79 reach a predetermined pressure at the start of the blood pressure measurement.

The air valve 32 is configured to maintain or reduce the pressure in the winding cuff 79 and opens or closes under control of an air valve drive circuit 37 in response to an instruction from the CPU 40. The air valve 32 maintains or reduces the pressure in the winding cuff 79 that has become high by the air pump 31 during the blood pressure measurement, and after the completion of the blood pressure calculation, rapidly exhausts air from the inside of the winding cuff 79 to return the inside of the winding cuff 79 to atmospheric pressure.

The pressure sensor 33 is configured to detect the pressure in the winding cuff 79. The pressure sensor 33 detects the pressure in the winding cuff 79 that varies with time from the start of the blood pressure measurement to when the completion of the blood pressure calculation and outputs a signal corresponding to the detected value to an amplifier 38.

The amplifier 38 amplifies the signal output from the pressure sensor 33 and outputs the signal thus amplified to an A/D converter 39. The A/D converter 39 converts the analog signal output from the amplifier 38 to digital form and outputs the digital signal to the CPU 40.

In this example, an output unit 42 includes the above-described display device 11 and printer 12.

In this example, an operation unit 43 includes the above-described power switch 10, measurement start/stop switches 13A, 13B, mode switch 13C, and measurement result displaying-stop switch 14.

T58*he* CPU 40 serves as a main control unit that performs main control including the blood pressure measurement, an air leakage testing unit that performs air leakage testing on the air systems 20, 30, and a notification control unit that performs notification control on the air leakage testing result. The CPU 40 outputs the blood pressure measurement result and the air leakage testing result to be described later to the display device 11 of the output unit 42 and a memory 41. Further, when a print instruction operation is made (for example, a print instruction switch (not illustrated) is pressed), the CPU 40 causes the printer 12 to print out the blood pressure measurement result on paper (in this example, roll paper). The mode switch 13C and the measurement result displaying-stop switch 14 will be described later.

The memory 41 serves as a storage unit and stores the blood pressure measurement result and the air leakage testing result.

Figure 5A:
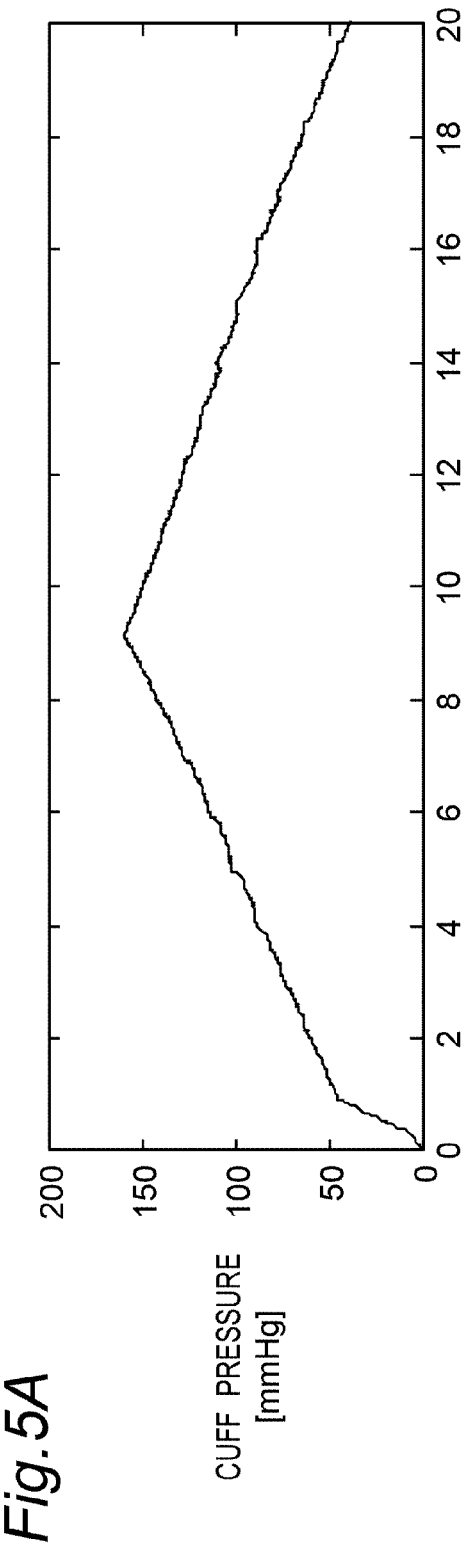
FIG. 5A is a diagram illustrating an example of a cuff pressure signal detected by a pressure sensor of the sphygmomanometer.
Figure 5B:
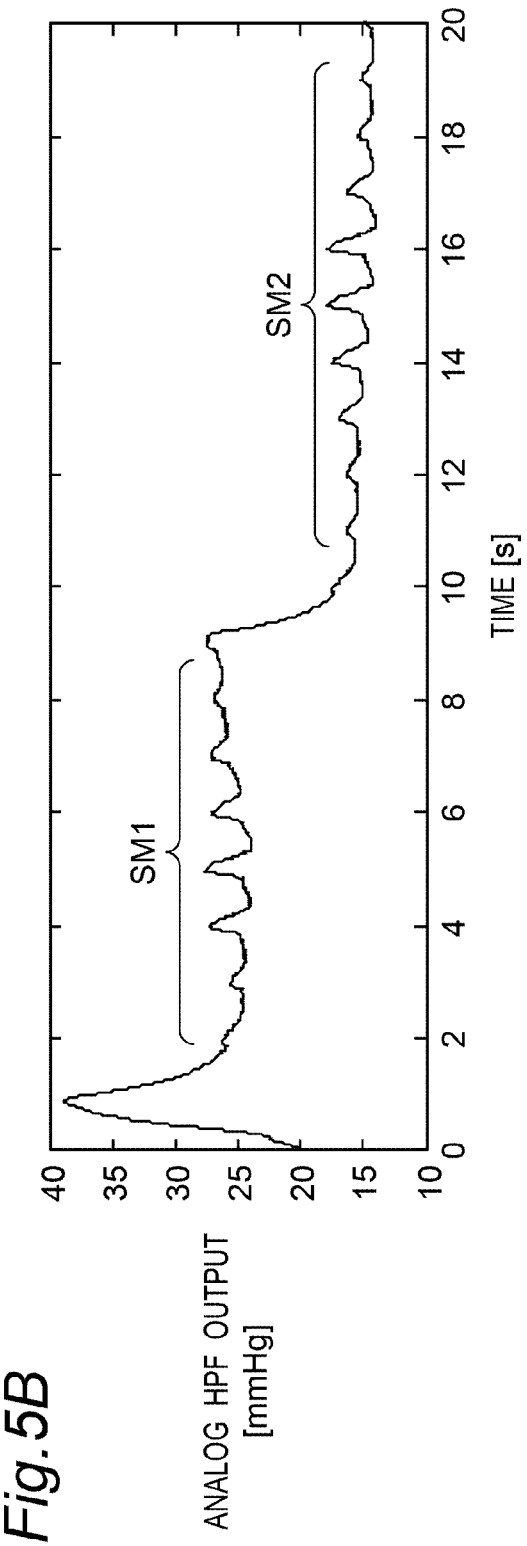
FIG. 5B is a diagram illustrating an example of a signal (HPF output) that is a component of the cuff pressure signal passing through a high-pass filter.

As illustrated in FIG. 5A, the pressure (cuff pressure) in the measurement cuff 77 detected by the pressure sensor 23 is a signal (cuff pressure signal) where a component that fluctuates with changes in arterial volume for each pulse is superimposed on pressure that increases (in a pressurization process) or decreases (in a depressurization process) approximately linearly with the lapse of time during the blood pressure measurement. A high-pass filter (HPF) is used to extract pulse waveforms (HPF outputs) SM1, SM2 as illustrated in FIG. 5B from the cuff pressure signal. As described later, in the sphygmomanometer 1, after an approximate maximum blood pressure (systolic blood pressure) is calculated by the oscillometric method based on the pulse waveform SM1 obtained in the pressurization process, the maximum blood pressure (systolic blood pressure) and the minimal blood pressure (diastolic blood pressure) are calculated with high accuracy based on the pulse waveform SM2 obtained in the depressurization process.

Main Control

Figure 4:
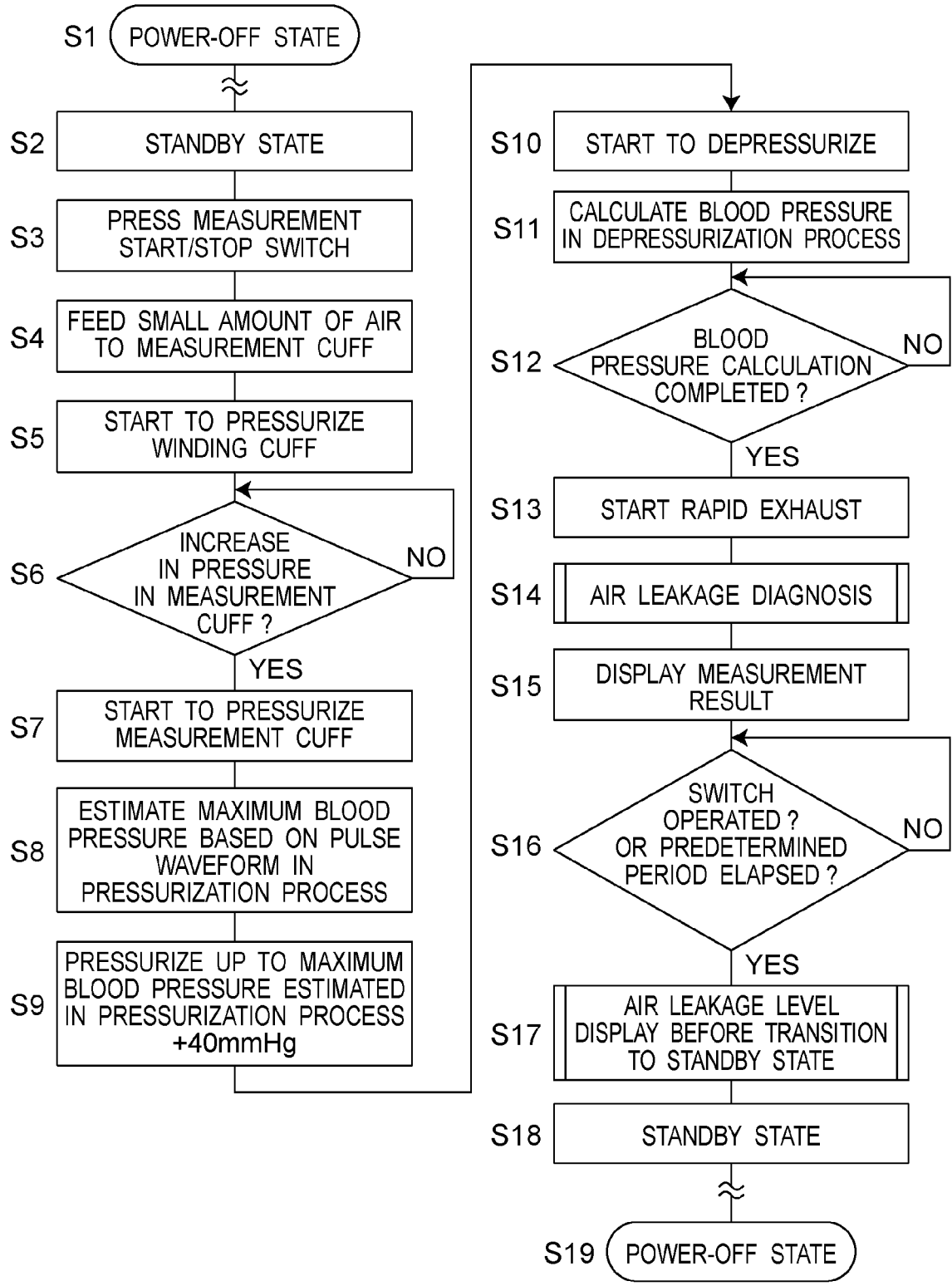
FIG. 4 is a diagram illustrating a flow of main control in the sphygmomanometer.

FIG. 4 illustrates a flow of the main control by the CPU 40 in the sphygmomanometer 1 having the above-described configuration. In this example, the main control includes blood pressure measurement processing by the oscillometric method and air leakage diagnosis processing as the air leakage testing.

Figure 15:
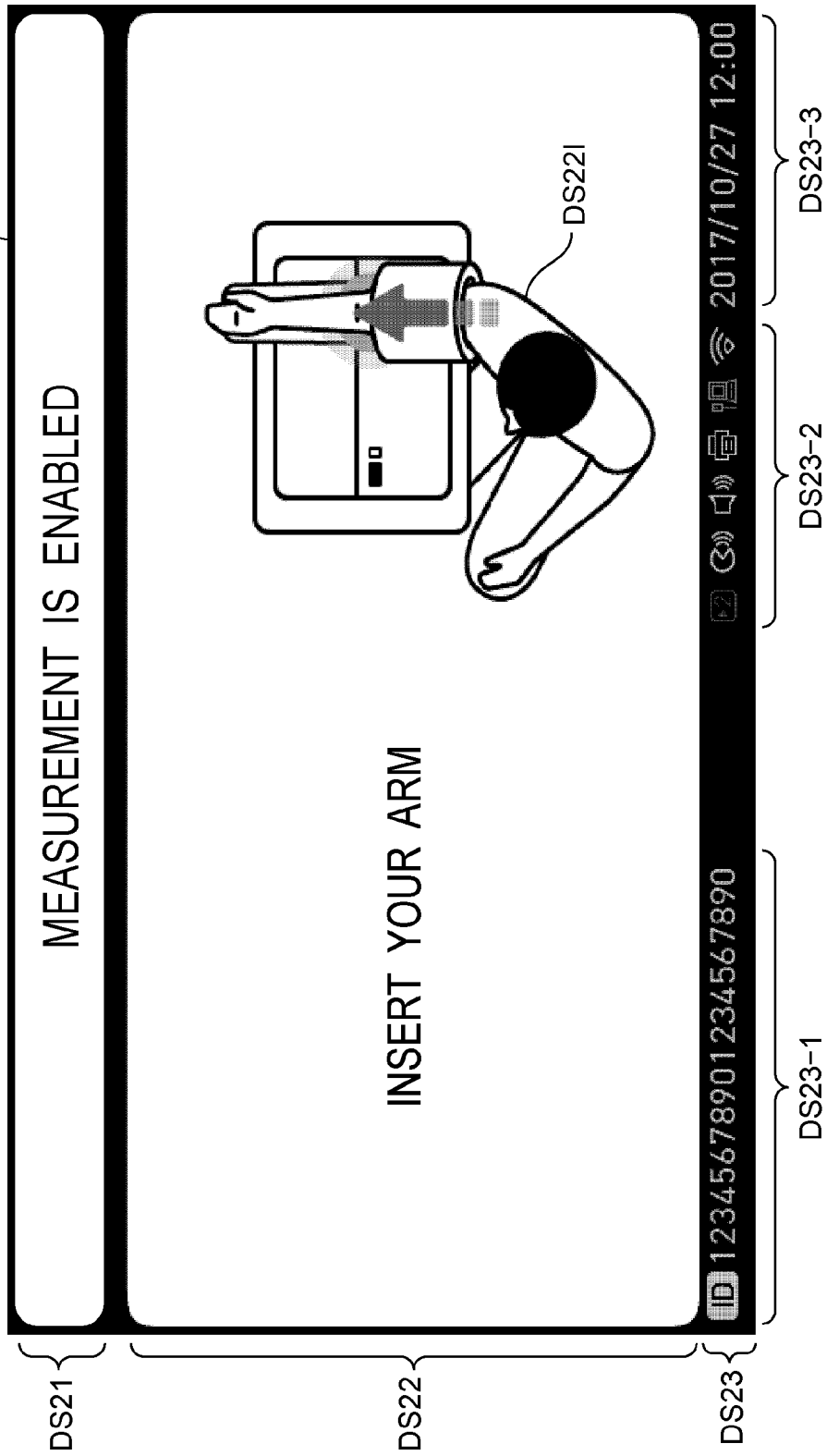
FIG. 15 is a diagram illustrating an example where, when the air leakage testing result is the second air leakage level, the air leakage testing result is not displayed.

First, in step S1 in FIG. 4, it is assumed that the sphygmomanometer 1 is in the power-off state. In the power-off state, the display device 11 is off (turned off) (the same applies hereinafter). In the power-off state, for example, when the power switch 10 is switched on by personnel of the hospital, the sphygmomanometer 1 is brought into the standby state through notification control on the air leakage testing result to be described in detail later (step S2). The "standby state" refers to a state of waiting for the measurement start switch (in this example, the measurement start/stop switch 13A) to be pressed, that is, a state where it is ready to perform the blood pressure measurement when the measurement start switch is pressed as the measurement start operation. In this example, in the standby state, the same display as illustrated in FIG. 15 to be described later is made on the display device 11. A general patient who is the subject usually would see the sphygmomanometer 1 only when the sphygmomanometer 1 is in the standby state or is in operation for the blood pressure measurement.

Next, when the subject presses the measurement start/stop switch 13A provided on the main body 2 in a condition where his/her upper arm 90 is inserted through the cuff 3 (cuff unit 5) (step S3), the sphygmomanometer 1 is brought into blood pressure measurement operation.

When brought into the blood pressure measurement operation, the sphygmomanometer 1 is first initialized. At this time, in the cuff unit 5 (cuff frame 7), as shown in FIG. 2A, the pressure in the measurement cuff 77 and the pressure in the winding cuff 79 are both equal to zero (atmospheric pressure). In this state (natural state), the circumferential ends of the curler 78 overlap each other, and the circumferential ends of the measurement cuff 77 relatively largely separate from each other.

Next, in step S4 in FIG. 4, the CPU 40 serves as a pressure control unit to feed a small amount of air (in this example, with a flow rate kept constant only for 250 milliseconds) from the air pump 21 to the measurement cuff 77 through the fluid pipe 81. This is because a timing at which the pressurization to the winding cuff 79 is to be stopped is detected based on an increase in pressure in the measurement cuff 77 in the subsequent step S6.

Figure 2B:
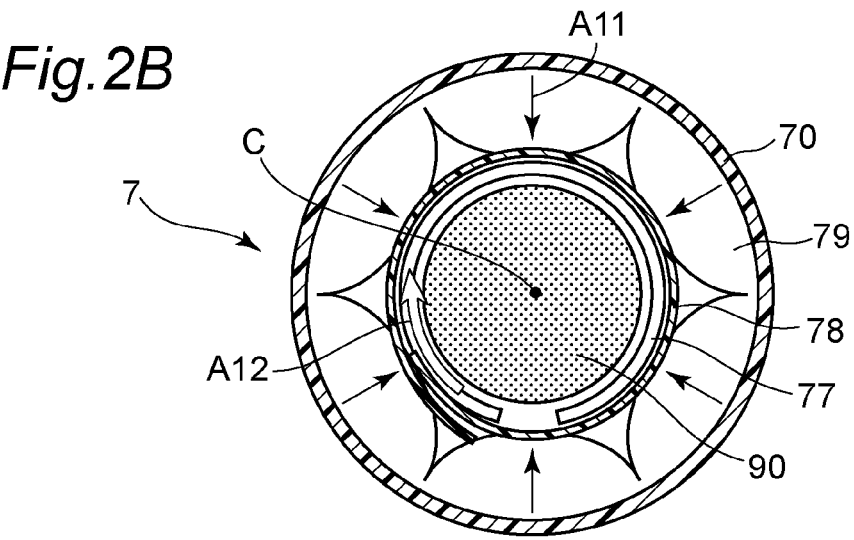
Figure 2C:
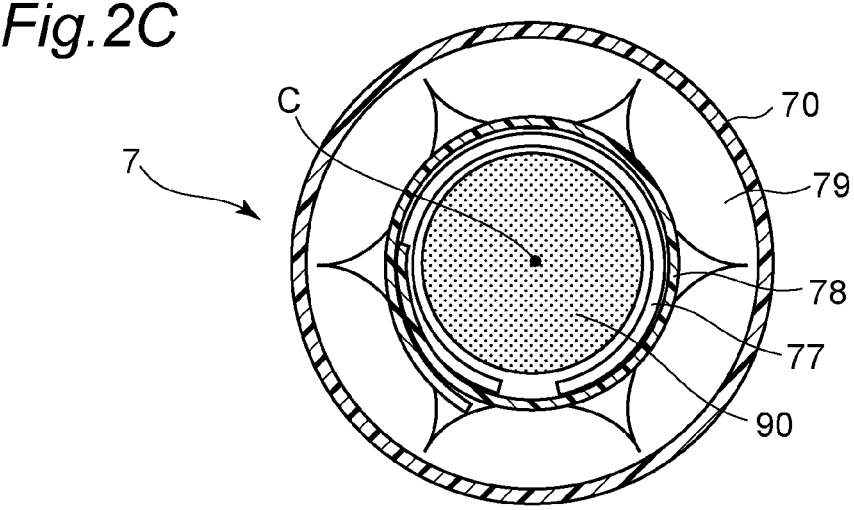

Next, in step S5 in FIG. 4, the CPU 40 serves as a pressure control unit to feed air from the air pump 31 to the winding cuff 79 through the fluid pipe 82. This starts pressurization of the winding cuff 79. At this time, in the cuff unit 5 (cuff frame 7), as indicated by an arrow A11 in FIG. 2B, the winding cuff 79 expands radially inward to compress the curler 78 radially inward. This makes the curler 78 smaller in diameter, makes the overlapping degree of the circumferential ends of the curler 78 larger as indicated by an arrow A12, and makes the circumferential ends of the measurement cuff 77 closer to each other. Then, when the pressure in the measurement cuff 77 reaches a predetermined pressure (in this example, 20 mmHg), the pressurization to the winding cuff 79 is stopped (step S6 in FIG. 4). As a result, as illustrated in FIG. 2C, the upper arm 90 is surrounded by the measurement cuff 77.

Next, in step S7 in FIG. 4, the CPU 40 serves as a pressure control unit to feed air from the air pump 21 to the measurement cuff 77 through the fluid pipe 81. This starts pressurization of the measurement cuff 77. Based on the pulse waveform SM1 (see FIG. 5B) obtained in this pressurization process, an approximate maximum blood pressure (systolic blood pressure) is calculated (estimated) by the oscillometric method (step S8 in FIG. 4). The measurement cuff 77 is kept pressurized up to the pressure in the measurement cuff 77 reaches a pressure where 40 mmHg is added to the maximum blood pressure thus calculated, that is, until the blood flowing through the arteries of the upper arm 90 fully stops (step S9 in FIG. 4). Then, the air pump 21 is stopped.

Next, in step S10 in FIG. 4, the CPU 40 serves as a pressure control unit to gradually exhaust air from the inside of the measurement cuff 77 through the fluid pipe 81 and the air valve 22 and to gradually exhaust air from the inside of the winding cuff 79 through the fluid pipe 82 and the air valve 32. This starts depressurization of the measurement cuff 77 and the winding cuff 79 under. In this example, a depressurization rate of the measurement cuff 77 and a depressurization rate of the winding cuff 79 are both set to 5 mmHg/second. The maximum blood pressure (systolic blood pressure) and the minimal blood pressure (diastolic blood pressure) are calculated by the oscillometric method based on the pulse waveform SM2 (see FIG. 5B) obtained in this depressurization process (steps S11, S12 in FIG. 4). At the same time, in this example, the CPU 40 serves as an air leakage testing unit to obtain a pressure difference (denoted by ΔP) between the pressure in the winding cuff 79 and the pressure in the measurement cuff 77 obtained at a time when the blood pressure calculation is completed. Note that it is assumed that a certain degree of pressure remains in both the winding cuff 79 and the measurement cuff 77 until the time of completion of the blood pressure calculation. The CPU 40 causes the memory 41 to store the pressure difference ΔP obtained at the time of completion of the blood pressure calculation in addition to the blood pressure measurement result (the maximum blood pressure and the minimal blood pressure) and the pulse rate.

After the completion of the blood pressure calculation, in step S13 in FIG. 4, the CPU 40 fully opens the air valves 22, 32 to rapidly exhaust air from the winding cuff 79 and the measurement cuff 77. This releases the pressure from the winding cuff 79 and the measurement cuff 77. At the same time, in this example, the CPU 40 serves as an air leakage testing unit to perform the air leakage diagnosis processing as the air leakage testing to be described later (step S14).

Next, in step S15 in FIG. 4, the CPU 40 displays, on the display device 11, the blood pressure measurement result (the maximum blood pressure and the minimal blood pressure) and the pulse rate. This allows the subject to know the blood pressure measurement result (the maximum blood pressure and the minimal blood pressure) and the pulse rate (the completion of the blood pressure measurement).

Next, in step S16 in FIG. 4, for example, when the measurement result displaying-stop switch 14 is pressed by the general patient as the subject (or personnel of the hospital) or a predetermined period (for example, 1 minute) elapses (YES in step S16), the CPU 40 serves as a notification control unit to perform air leakage level display processing before a transition to the standby state to be described later as a part of the notification control (step S17).

Subsequently, the sphygmomanometer 1 usually (unless the air leakage is at a failure level) makes a transition to the standby state (step S18). In this example, in the standby state, the same display as illustrated in FIG. 15 to be described later is made on the display device 11. In this standby state, for example, when the power switch 10 is switched off as a power-off operation by the personnel of the hospital, the sphygmomanometer 1 returns to the power-off state through notification control on the air leakage testing result to be described in detail later (step S19).

Note that the CPU 40 performs the air leakage testing on the air systems 20, 30 in conjunction with the blood pressure measurement and causes, for each air leakage testing, the memory 41 to store the pressure difference ΔP obtained at the time of completion of the blood pressure calculation in addition to the blood pressure measurement result (the maximum blood pressure and the minimal blood pressure) and the pulse rate.

Air Leakage Diagnosis Processing

The air leakage diagnosis processing (step S14 in FIG. 4) in the sphygmomanometer 1 is set based on findings that most of the failure cases are caused by air leakage from the winding cuff 79 for a type of sphygmomanometer including the above-described cuff unit 5.

Figure 6:
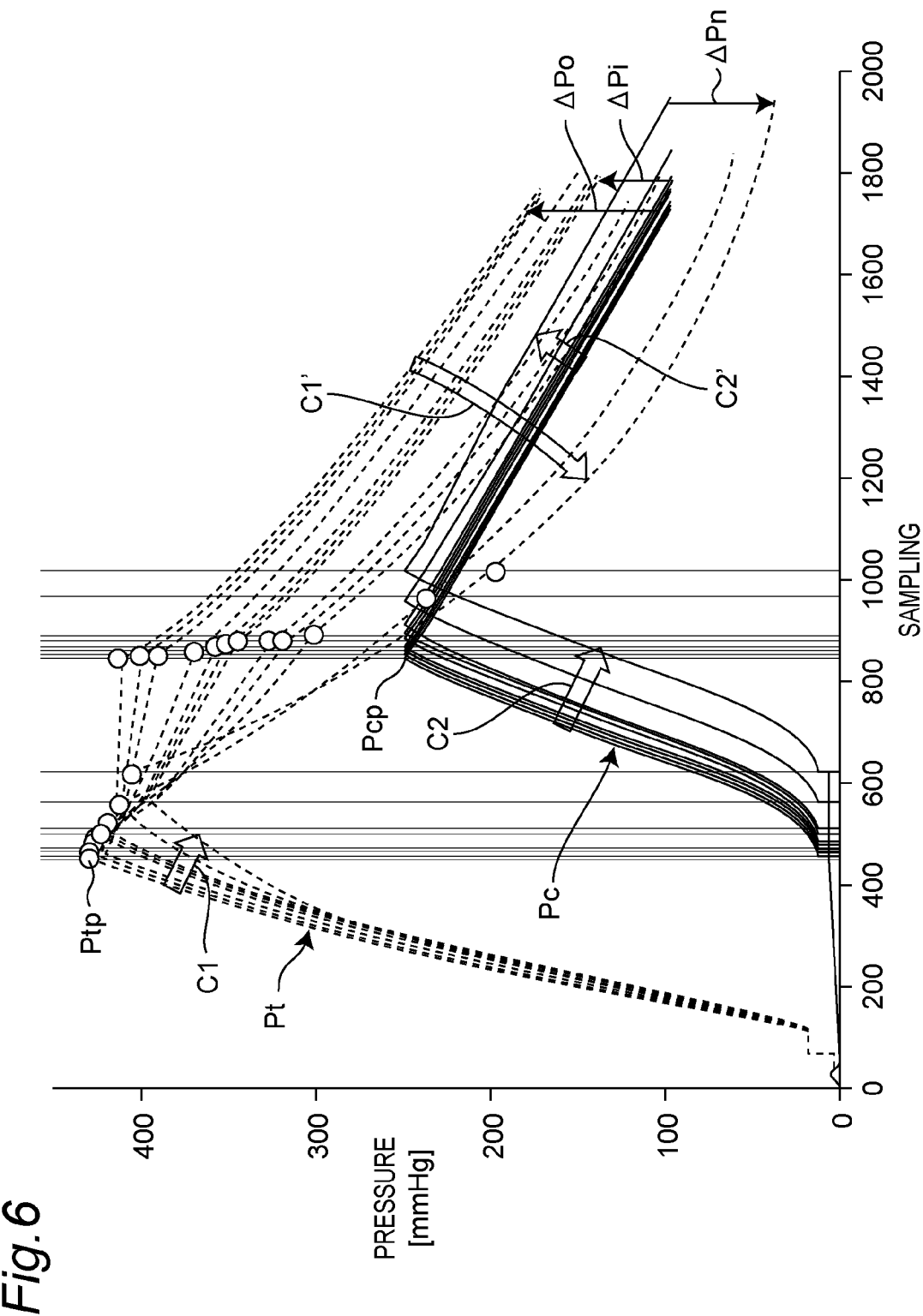
FIG. 6 is a diagram illustrating changes in pressure, during blood pressure measurement, in a winding cuff and measurement cuff included in the air system of a sphygmomanometer identical in configuration to the above-described sphygmomanometer.

Specifically, FIG. 6 illustrates changes in pressure, during the blood pressure measurement, in the winding cuff 79 and the measurement cuff 77 in a sphygmomanometer identical in configuration to the sphygmomanometer 1 (a horizontal axis represents a number of sampling of pressure during each blood pressure measurement). During each blood pressure measurement, pressure Pt in the winding cuff 79 rises, as indicated by a dashed line in FIG. 6, when pressurized (steps S5 and S6 in FIG. 4), reaches a peak Ptp, and then falls. Pressure Pc in the measurement cuff 77 rises, as indicated by a solid line in FIG. 6, in the pressurization process (steps S7 to S9 in FIG. 4), reaches a peak Pcp, and then falls. When the blood pressure measurement is repeated a plurality of times (in this example, about 1000 times), the rising speed of the pressure Pt in the winding cuff 79 gradually decreases as indicated by an arrow C1 in FIG. 6, and the falling speed gradually increases as indicated by an arrow C1' due to a gradual increase in air leakage. On the other hand, the rising speed of the pressure Pc in the measurement cuff 77 gradually decreases as indicated by an arrow C2 in FIG. 6, but the falling speed of the pressure applied by the winding cuff 79 via the curler 78 gradually increases, so that the falling speed of the pressure Pc gradually decreases as indicated by an arrow C2'.

Therefore, in the sphygmomanometer 1, the air leakage testing result is obtained based on the pressure difference ΔP between the pressure Pt in the winding cuff 79 and the pressure Pc in the measurement cuff 77 obtained at the time of completion of the blood pressure calculation in the depressurization process during the blood pressure measurement (step S12 in FIG. 4). For example, the pressure difference ΔP represents a positive value as indicated by an arrow ΔPo in FIG. 6 at the beginning of the repetition of the blood pressure measurement. When the number of repetitions increases, the value gradually decreases as indicated by an arrow ΔPi in FIG. 6, and represents, in an extreme case, a negative value as indicated by an arrow ΔPn in FIG. 6. This allows air leakage from the winding cuff 79 to be detected based on the pressure Pc in the measurement cuff 77.

Figure 7:
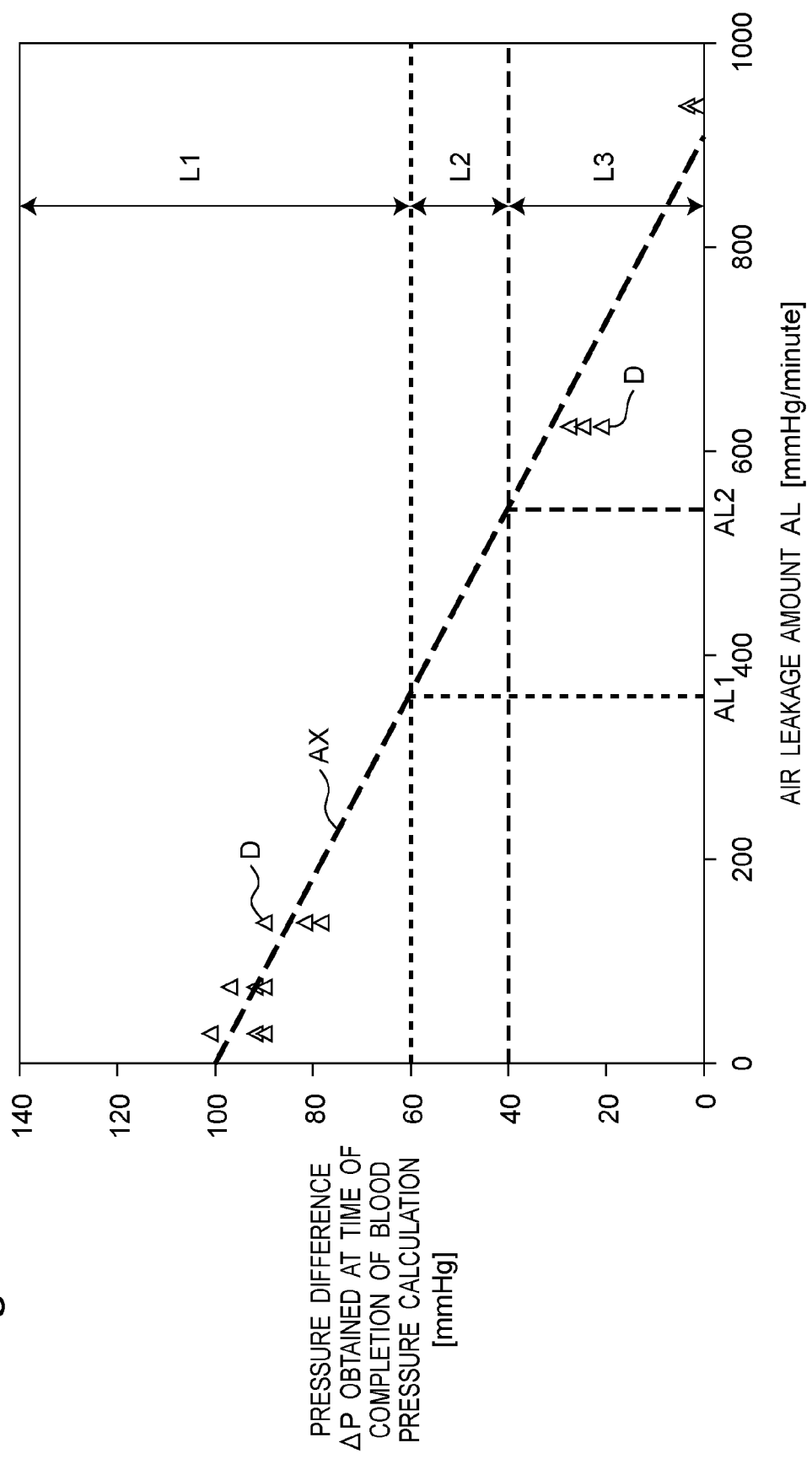
FIG. 7 is a scatter diagram illustrating a relationship between a pressure difference between a pressure in the above-described winding cuff and a pressure in the above-described measurement cuff obtained at a time when a blood pressure calculation is completed and an air leakage amount actually measured only for a winding air system.

Further, FIG. 7 illustrates, as a scatter diagram, a relationship between the pressure difference ΔP (mmHg), actually measured for a sphygmomanometer identical in configuration to the sphygmomanometer 1, at the time of completion of the blood pressure calculation and an air leakage amount AL (mmHg/minute) actually measured only for the winding air system 30. Triangle marks Δ in FIG. 7 indicate individual actually measured data D. Specifically, the air leakage amount AL indicated by certain measured data D in FIG. 7 is an amount actually measured under a configuration of the winding air system 30 illustrated in FIG. 3 where an air tank (having a capacity of 500 cc) is attached instead of the winding cuff 79, a leak valve (adjustable in leak flow rate) configured to cause air to escape from the air system 30 to the atmosphere is attached to a position where the fluid pipe 82 is located, and a leak flow rate of the leak valve is set to a certain value (denoted by Lx1). In the first step of this measurement, the winding air system 30 is pressurized to 400 mmHg. Immediately after the pressurization, the pressure decreases due to changes in temperature caused by air compression, and thus the pressure stable is required to be waited for at least 15 seconds. Subsequently, with the leak flow rate of the leak valve maintained at a certain level, a decrease in the pressure is observed for 1 minute to obtain the air leakage amount AL (mmHg/min). On the other hand, the pressure difference ΔP indicated by the measured data D in FIG. 7 corresponds to an amount actually measured at the time of completion of the blood pressure calculation after the blood pressure measurement for a sphygmomanometer identical in configuration to the sphygmomanometer 1 with the leak valve attached to a position where the fluid pipe 82 is located and the leak flow rate of the leak valve set to a value Lx1 the same as described above. The plurality of pieces of measured data D illustrated in FIG. 7 are each obtained with the leak valve set adjustable in leak flow rate to various values (for example, Lx1, Lx2, Lx3, . . . ) in the same procedure.

As can be seen from an approximate straight line AX illustrated in FIG. 7, the pressure difference ΔP measured at the time of completion of the blood pressure calculation and the air leakage amount AL measured only for the winding air system 30 indicate a strong negative correlation.

Therefore, in the sphygmomanometer 1, as the air leakage testing result, a first air leakage level L1 representing that the air leakage amount AL of the air systems 20, 30 (mainly, the air system 30, and the same applies hereinafter) is less than a predetermined first reference value AL1, a third air leakage level L3 representing that the air leakage amount AL of the air systems 20, 30 is greater than a second reference value AL2 set greater than the first reference value AL1, and a second air leakage level L2 corresponding to the air leakage amount AL of the air systems 20, 30 in a range between the first reference value AL1 and the second reference value AL2 are set. The first air leakage level L1 corresponds, in this example, to a normal level including a case where there is no air leakage. In this example, the third air leakage level L3 corresponds to a failure level, that is, a level at which the blood pressure measurement can no longer be performed by the sphygmomanometer. The second air leakage level L2 corresponds to a level between the first air leakage level L1 and the third air leakage level L3, that is, an initial stage where air has just started to leak from the air systems 20, 30.

Specifically, in this example, the first reference value AL1 corresponds to a pressure difference ΔP of 60 mmHg, and the first air leakage level L1 corresponds to a pressure difference ΔP of greater than 60 mmHg (i.e. ΔP>60 mmHg). The second reference value AL2 corresponds to a pressure difference ΔP of 40 mmHg, and the third air leakage level L3 corresponds to a pressure difference ΔP of 40 mmHg or less (i.e. ΔP≤40 mmHg). The second air leakage level L2 corresponds to a pressure difference ΔP greater than 40 mmHg and equal to or less than 60 mmHg (i.e. 40 mmHg<ΔP≤60 mmHg).

Under such settings, the above-described air leakage diagnosis processing (step S14 in FIG. 4) is performed as follows. That is, the CPU 40 serves as an air leakage testing unit to start air leakage diagnosis in step S20 in FIG. 8. First, in step S21, the CPU 40 reads the latest pressure difference ΔP obtained at the time of completion of the blood pressure calculation and stored in the memory 41, and determines whether or not the pressure difference ΔP thus read is greater than 60 mmHg corresponding to the first reference value AL1, and whether or not the pressure difference ΔP thus read is greater than 40 mmHg corresponding to the second reference value AL2. When the pressure difference ΔP is greater than 60 mmHg (i.e. ΔP>60 mmHg), it is determined that the air leakage level of the air systems 20, 30 is the first air leakage level L1 (step S22). When the pressure difference ΔP is greater than 40 mmHg and equal to or less than 60 mmHg (i.e. 40 mmHg<Δ≤60 mmHg), it is determined that the air leakage level of the air systems 20, 30 is the second air leakage level L2 (step S23). When the pressure difference ΔP is equal to or less than 40 mmHg (i.e. ΔP≤40 mmHg), it is determined that the air leakage level of the air systems 20, 30 is the third air leakage level L3 (step S24). In any of the cases, the CPU 40 stores the air leakage level L1, L2, or L3 in the memory 41 and brings the air leakage diagnosis processing to an end (step S25).

Each time the above-described air leakage diagnosis processing (FIG. 8) is performed in conjunction with the blood pressure measurement, the memory 41 stores the latest air leakage levels L1, L2, or L3 as the air leakage testing result. Note that, in a stage where the sphygmomanometer 1 has never performed the blood pressure measurement at all (for example, immediately after the sphygmomanometer 1 is assembled or at a stage before product shipment testing), the air leakage level L1 is stored in the memory 41 as a default.

Notification Control

In the sphygmomanometer 1, the CPU 40 serves as a notification control unit to perform notification control on the air leakage testing result in the following five transitions. This notification control is performed based on the latest air leakage level stored in the memory 41.

Figure 9:
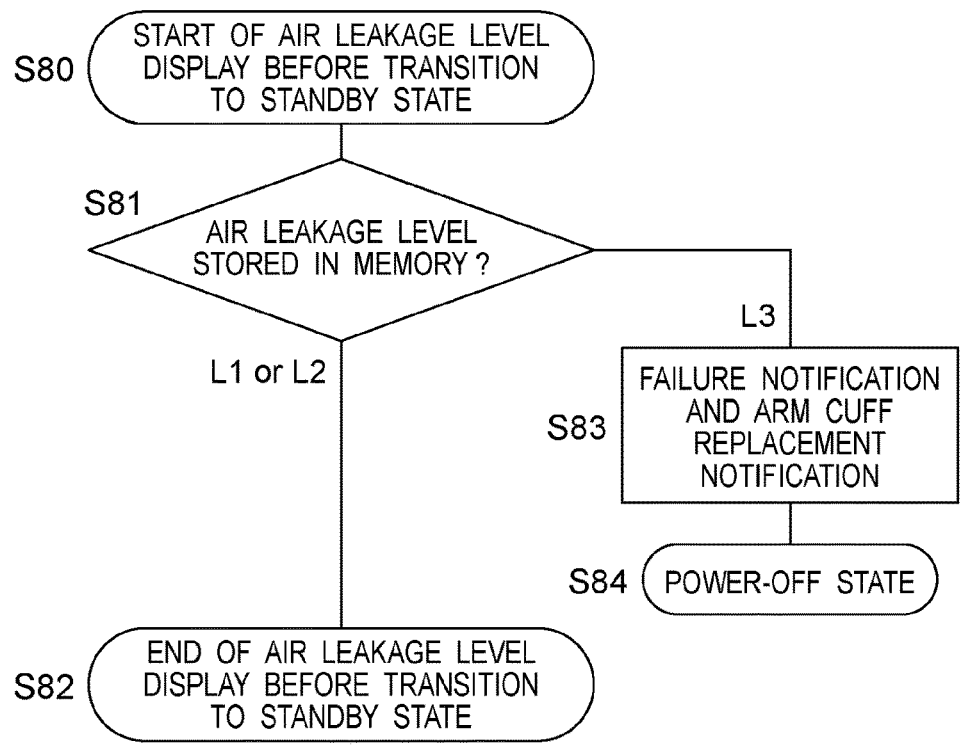
FIG. 9 is a diagram illustrating a flow of notification control (air leakage level display processing before a transition to a standby state) during a transition from the end of blood pressure measurement to the standby state in the sphygmomanometer.

(1) Notification Control During Transition from End of Blood Pressure Measurement to Standby State FIG. 9 illustrates a detailed flow of the above-described air leakage level display processing (step S17 in FIG. 4) before the transition to the standby state as notification control during the transition from the end of the blood pressure measurement to the standby state in the sphygmomanometer 1. In this example, the CPU 40 serves as a notification control unit to start the air leakage level display processing before the transition to the standby state in step S80 in FIG. 9. First, the CPU 40 reads the latest air leakage level stored in the memory 41 and determines whether the air leakage level thus read is L1, L2, or L3 (step S81). When the air leakage level is L1 or L2, the CPU 40 directly makes a transition to the standby state without displaying the air leakage testing result (step S82). As a result, during the transition from the end of the blood pressure measurement to the standby state in the sphygmomanometer 1, it is possible to prevent the general patient from noticing the air leakage testing result (here, the air leakage levels L1, L2). On the other hand, when the air leakage level is L3, the CPU 40 makes displaying, on the display device 11, an indication that the blood pressure measurement is disabled (failure notification and arm cuff replacement notification) immediately (that is, even at a timing when the general patient would see the sphygmomanometer 1) (step S83). Subsequently, the CPU 40 brings the sphygmomanometer 1 into the power-off state for safety (step S84).

FIGS. 18A and 18B illustrate display examples on the display device 11 in step S83 in FIG. 9. In a display example DS7 illustrated in FIG. 18A, a message "Contact the administrator" is displayed in an upper section DS71, and the meaning and code of an error code "Arm cuff replacement error E6" are displayed in a lower section DS72 (dot matrix mode). In a display example DS8 illustrated in FIG. 18B, only the error code "E6" is displayed (segment mode). In this example, the error code "E6" indicates a failure of the arm cuff (cuff unit 5) due to air leakage. Such a display prevents the general patient from pressing the measurement start switch in vain to perform the blood pressure measurement.

Figure 10:
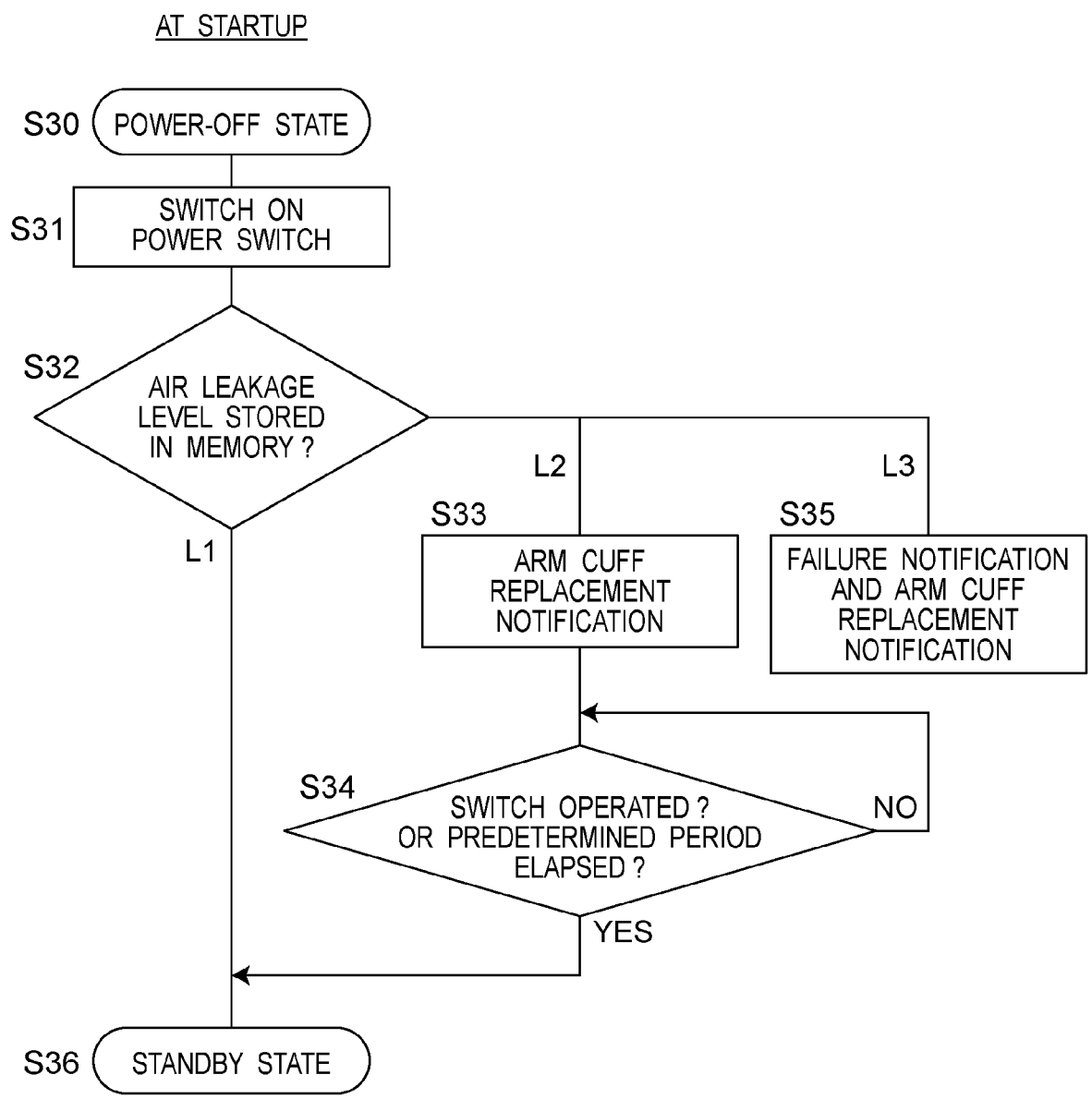
FIG. 10 is a diagram illustrating a flow of notification control during a transition from a power-off state to the standby state in (at the startup of) the sphygmomanometer.

(2) Notification Control During Transition from Power-Off State to Standby State FIG. 10 illustrates a flow of notification control during the transition from the power-off state to the standby state in (at the startup of) the sphygmomanometer 1. In this example, in the first step S30 in FIG. 10, it is assumed that the sphygmomanometer 1 is in the power-off state as in step S1 in FIG. 4. In this power-off state, for example, when the power switch 10 is switched on by the personnel of the hospital (step S31 in FIG. 10), the CPU 40 reads the latest air leakage level stored in the memory 41 and determines whether the air leakage level thus read is L1, L2, or L3 (step S32). When the air leakage level is L1, the CPU 40 directly makes a transition to the standby state without displaying the air leakage testing result (step S36). In the standby state (step S36) to which a transition is made when the air leakage level is L1, the air leakage testing result is not displayed, and a display in the normal standby state (the same as a display example illustrated in FIG. 15 to be described later) is displayed on the display device 11 in this example.

Further, when the air leakage level is L3 in step S32 in FIG. 10, the CPU 40 makes displaying, on the display device 11, an indication that the blood pressure measurement is disabled (failure notification and arm cuff replacement notification) (step S35). The indication that the blood pressure measurement is disabled is the same as illustrated in FIG. 18A or 18B, for example. The personnel of the hospital can recognize, by viewing this display, that a failure has occurred and that the arm cuff (in this example, the cuff unit 5) needs to be replaced. Note that no transition from step S35 in FIG. 10 to the standby state is made. This prevents the general patient from pressing the measurement start switch in vain to perform the blood pressure measurement.

Figure 14:
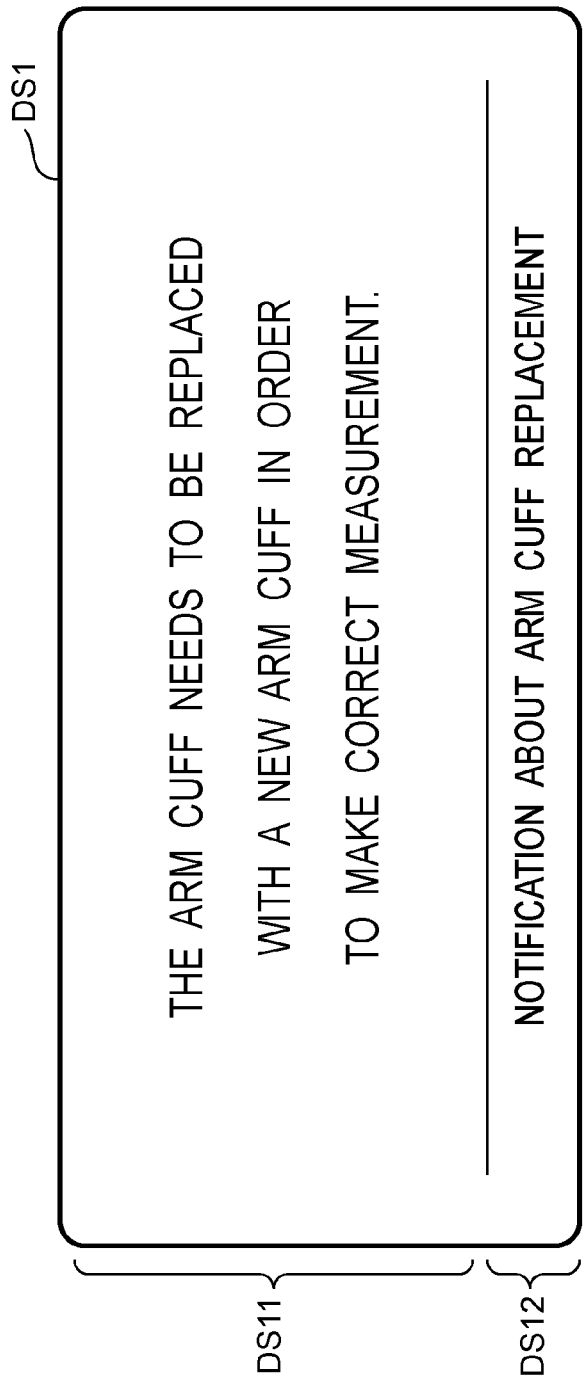
FIG. 14 is a diagram illustrating a display example in a first display mode including a message indicating a measure against an air leakage testing result when the air leakage testing result is a second air leakage level.

When the air leakage level is L2 in step S32 in FIG. 10, the CPU 40 makes displaying, on the display device 11, the arm cuff replacement notification as the air leakage testing result in a first display mode (step S33). For example, FIG. 14 illustrates a display example DS1 in the first display mode in step S33 in FIG. 10 (dot matrix mode). In the display example DS1, a message "The arm cuff needs to be replaced with a new arm cuff in order to make correct measurement." indicating a measure against the air leakage testing result is displayed in the upper section DS11, and a title "Notification about arm cuff replacement" is displayed in the lower section DS12. Thereby, the air leakage testing result is displayed on the display device 11 at a timing when the general patient would not see the sphygmomanometer 1. The personnel of the hospital can easily recognize the air leakage testing result by viewing the air leakage testing result displayed in the first display mode on the display device 11 (FIG. 14) and take a measure indicated by the message. In this example, the personnel of the hospital can notice that it is an initial stage where air has just started to leak from the air systems 20, 30. This allows the personnel of the hospital (particularly, maintenance personnel) to replace a component of the air systems 20, 30 (in this example, the cuff unit 5) or prepare a component for replacement. This in turn makes it possible to prevent a failure from occurring, or, even when a failure occurs, this makes it possible to shorten, by immediately replacing a corresponding component with a new component, a time during which the blood pressure measurement is disabled.

After having started to make displaying the air leakage testing result in the first display mode (FIG. 14) (step S33 in FIG. 10), when the measurement start/stop switch 13A serving as a display stop switch is pressed, or a predetermined period (for example, 1 minute) elapses (YES in step S34 in FIG. 10), the CPU 40 makes a transition to the standby state (step S36). Thereby, the CPU 40 stops the displaying the air leakage testing result in the first display mode (FIG. 14). Therefore, it is guaranteed that the displaying the air leakage testing result in the first display mode is only temporarily provided. For example, after the displaying the air leakage testing result in the first display mode has been started, even when the personnel of the hospital forgets to press the display stop switch (measurement start/stop switch 13A), it is possible to prevent the general patient from noticing the air leakage testing result.

In the standby state (step S36) to which a transition is made from step S33 through step S34 in FIG. 10, for example, the CPU 40 does not display the air leakage testing result but makes displaying, on the display device 11, a display in the normal standby state as illustrated in FIG. 15. In the display example DS2 illustrated in FIG. 15, a message "Measurement is enabled" is displayed in the upper section DS21, and a message "Insert your arm" and an illustration DS22I indicating a measurement posture are displayed in a middle section DS22. Further, in the lower section DS23, an area DS23-1 where a measurement number appears, an area DS23-2 where various icons representing the state of the sphygmomanometer 1 appear, and an area DS23-3 where the current date appears. In the display example DS2, since no air leakage testing result is displayed, the general patient would not notice the air leakage testing result.

Instead of the display example DS2 in FIG. 15, for example, as illustrated in FIG. 16, the CPU 40 may make displaying the air leakage testing result in a second display mode lower in degree of enhancement than the first display mode (FIG. 14). A display example DS3 illustrated in FIG. 16 is different from the display example DS2 illustrated in FIG. 15 only in that an icon IC1 formed of an illustration representing a prompt to remove the cuff unit is additionally displayed in the area DS23-2 where the icon is to be displayed. Since the icon IC1 is merely an additional icon with respect to the plurality of other icons displayed in the area DS23-2, the icon IC1 is low in degree of enhancement for conveyance of the air leakage testing result and inconspicuous as compared with the display example DS1 including the message in the first display mode (FIG. 14). Therefore, the general patient who does not know the meaning of the icon IC1 would not notice the air leakage testing result. On the other hand, the personnel of the hospital (particularly, maintenance personnel) who knows the meaning of the icon IC1 can recognize the air leakage testing result by viewing the icon IC1 displayed on the display device 11 and take a measure suggested by the icon IC1.

In the standby state (step S36); regardless of which of the display example DS2 in FIG. 15 and the display example DS3 in FIG. 16 is displayed on the display device 11, the general patient who is the subject can perform the blood pressure measurement by pressing the measurement start/stop switch 13A in a condition where his/her upper arm 90 is inserted through the cuff 3 (cuff unit 5) (step S3 in FIG. 4), as in the standby state in step S2 in FIG. 4. During the blood pressure measurement (particularly, steps S4 to S15 in FIG. 4), the air leakage testing result is not displayed on the display device 11, or, even when it is displayed, the air leakage testing result is displayed in the second display mode (FIG. 16) lower in degree of enhancement than the first display mode (FIG. 14). This prevents the general patient from noticing the air leakage testing result.

Modification of Display

For example, as the first display mode, a display example DS4 of FIG. 17A may be used instead of the display example DS1 of FIG. 14. Further, as an example where the air leakage testing result is not displayed, a display example DS5 in FIG. 17B may be used instead of the display example DS2 in FIG. 15. Further, as the second display mode, a display example DS6 in FIG. 17C may be used instead of the display example DS3 in FIG. 16.

In the display example DS4 in FIG. 17A as the first display mode, the current date is displayed in an upper section DS40, the maximum blood pressure (mmHg) is displayed in a middle upper section DS41, the minimal blood pressure (mmHg) is displayed in a middle lower section DS42, and the pulse rate (pulse/minute) is displayed in a lower section DS43. Further, an area DS44 where various icons are to be displayed for indicating the state of the sphygmomanometer 1 is provided along the right side. In the display example DS4, the icon IC1 formed of an illustration representing a prompt to remove the cuff unit based on the air leakage testing result is displayed in a blinking manner at the lowermost portion of the area DS44 (note that a radial mark FL is merely illustrated for convenience in order to express the blinking icon IC1 and is not displayed on the actual display device 11). Thereby, the air leakage testing result is displayed on the display device 11 at a timing when the general patient would not see the sphygmomanometer 1. The blinking icon IC1 is conspicuous. The personnel of the hospital can easily recognize the air leakage testing result by viewing the air leakage testing result displayed in the first display mode (FIG. 17A) on the display device 11 and take a measure suggested by the icon IC1. In this example, the personnel of the hospital can notice that it is an initial stage where air has just started to leak from the air systems 20, 30. This allows the personnel of the hospital (particularly, maintenance personnel) to replace a component of the air systems 20, 30 (in this example, the cuff unit 5) or prepare a component for replacement. This in turn makes it possible to prevent a failure from occurring, or, even when a failure occurs, this makes it possible to shorten, by immediately replacing a corresponding component with a new component, a time during which the blood pressure measurement is disabled.

The display example DS5 illustrated in FIG. 17B as an example where the air leakage testing result is not displayed is different from the display example DS4 in FIG. 17A only in that there is no icon IC1. In the display example DS5, since the air leakage testing result is not displayed, the general patient would not notice the air leakage testing result.

The display example DS6 illustrated in FIG. 17C as the second display mode is different from the display example DS4 in FIG. 17A only in that the icon IC1 is kept lit. Since the icon IC1 is kept lit, the icon IC1 is lower in degree of enhancement than the blinking icon IC1 illustrated in FIG. 17A and is thus inconspicuous. Therefore, the general patient who does not know the meaning of the icon IC1 would not notice the air leakage testing result. On the other hand, the personnel of the hospital (particularly, maintenance personnel) who knows the meaning of the icon IC1 can recognize the air leakage testing result by viewing the icon IC1 displayed on the display device 11 and take a measure suggested by the icon IC1.

Figure 11:
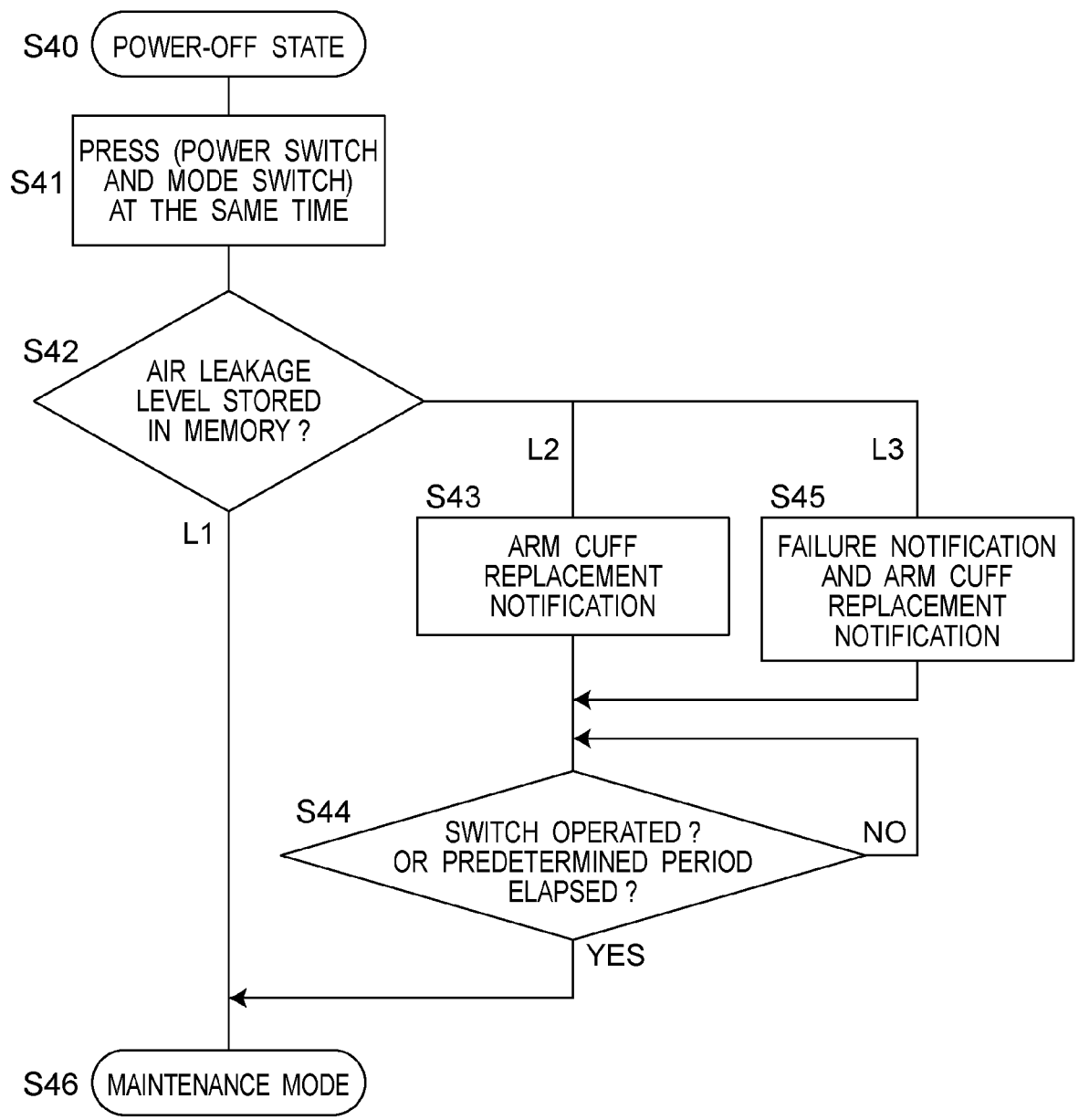
FIG. 11 is a diagram illustrating a flow of notification control during a transition from the power-off state to a maintenance mode (during a transition to maintenance) in the sphygmomanometer.

(3) Notification Control During Transition from Power-Off State to Maintenance Mode FIG. 11 illustrates a flow of notification control during the transition from the power-off state to the maintenance mode as the non-blood pressure measurement state where the measurement start operation is disabled (during the transition to maintenance) in the sphygmomanometer 1. The maintenance mode is a mode where maintenance of the sphygmomanometer 1 is performed, and various functions are checked or fixed.

In this example, in the first step S40 in FIG. 11, it is assumed that the sphygmomanometer 1 is in the power-off state as in step S1 in FIG. 4. In this power-off state, for example, when the power switch 10 and the mode switch 13C are switched on at the same time by the personnel of the hospital (step S41 in FIG. 11), the CPU 40 reads the latest air leakage level stored in the memory 41 and determines whether the air leakage level thus read is L1, L2, or L3 (step S42). When the air leakage level is L1, as in the example in FIG. 10, the CPU 40 directly makes a transition to the maintenance mode without displaying the air leakage testing result (step S46).

Further, when the air leakage level is L3 in step S42 in FIG. 11, the CPU 40 makes displaying, on the display device 11, an indication that the blood pressure measurement is disabled (failure notification and arm cuff replacement notification) (step S45), as in the example in FIG. 10. The display indicating that the blood pressure measurement is disabled is the same as illustrated in FIG. 18A or 18B. The personnel of the hospital can recognize, by viewing this display, that a failure has occurred and that the arm cuff (in this example, the cuff unit 5) needs to be replaced. Subsequently, the processing proceeds to step S44 in FIG. 11 to be described later.

When the air leakage level is L2 in step S42 in FIG. 11, the CPU 40 makes displaying, on the display device 11, the arm cuff replacement notification as the air leakage testing result in the first display mode (step S43). The display in the first display mode is the same as illustrated in FIG. 14 or 17A. The personnel of the hospital can recognize, by viewing this display, the air leakage testing result and take a necessary measure.

After having started to make displaying the air leakage testing result in the first display mode (FIG. 14 or 17A) (step S43 in FIG. 11) or after having started to make displaying the indication that the blood pressure measurement is disabled (FIG. 18A or 18B) (step S45 in FIG. 11), when the measurement start/stop switch 13A serving as a display stop switch is pressed, or the a predetermined period (for example, 1 minute) elapses (YES in step S44 in FIG. 11), the CPU 40 makes a transition to the maintenance mode (step S46). Thereby, the CPU 40 stops the displaying the air leakage testing result in the first display mode (FIG. 14 or 17A). Therefore, it is guaranteed that the displaying the air leakage testing result in the first display mode is only temporarily provided.

In the maintenance mode (step S46), a maintenance guide display (not illustrated) for facilitating maintenance is made on the display device 11. In accordance with the maintenance guide display, the personnel of the hospital (specifically, maintenance personnel) can perform maintenance of the sphygmomanometer 1. The general patient usually would not see the sphygmomanometer 1 in this maintenance mode.

(4) Notification Control During Transition from Standby State to Setting Mode

Figure 12:
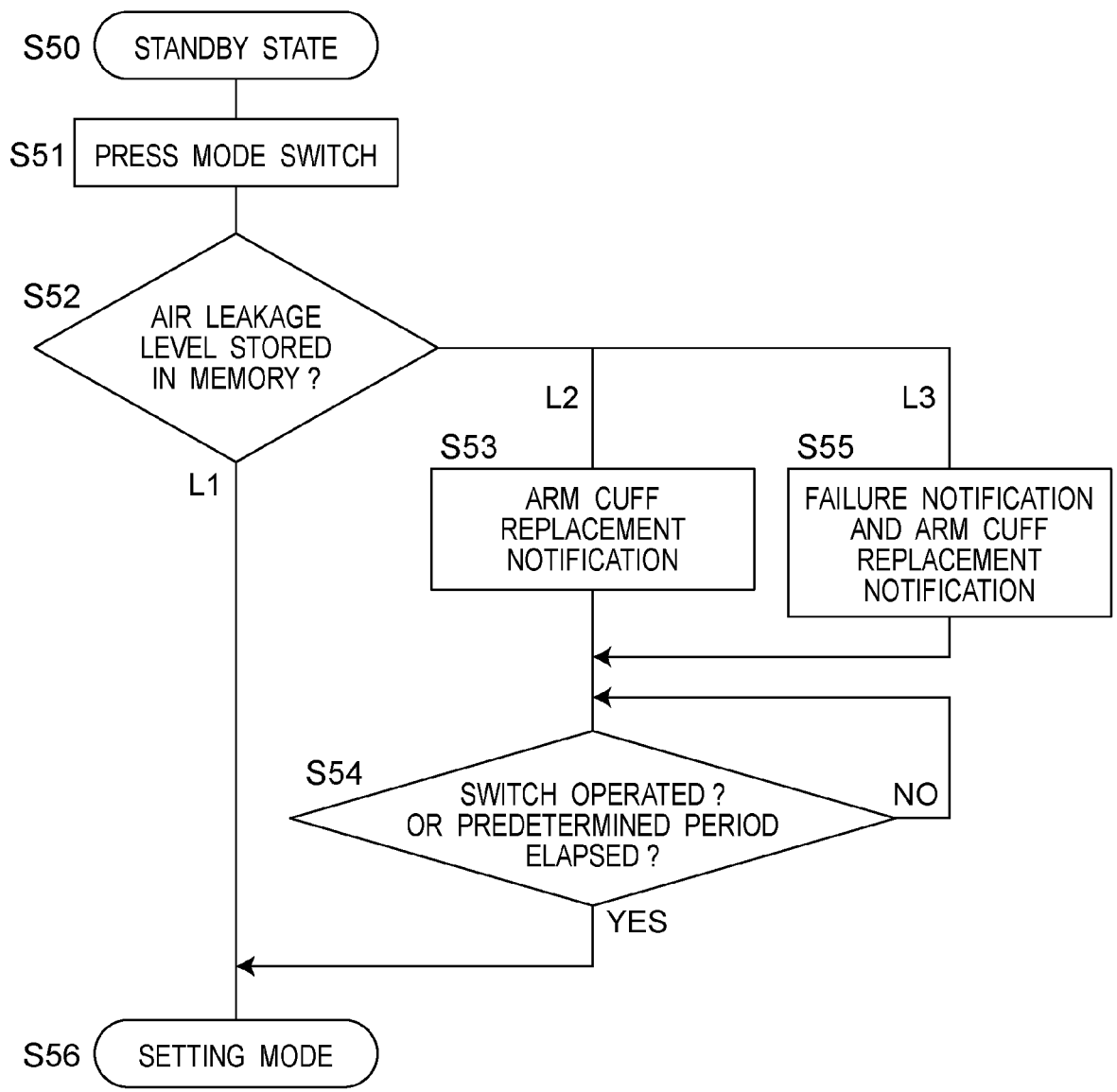
FIG. 12 is a diagram illustrating a flow of notification control during a transition from the standby state to a setting mode (during a transition to the setting mode) in the sphygmomanometer.

FIG. 12 illustrates a flow of notification control during the transition from the standby state to the setting mode as the non-blood pressure measurement state where the measurement start operation is disabled (during the transition to setting mode) in the sphygmomanometer 1. The setting mode is a mode where various settings that define the operation of the sphygmomanometer 1 are made. Examples of the setting items include a print content setting of the printer 12, a volume setting of voice guidance, a content setting of voice guidance, and the like.

In this example, it is assumed that the sphygmomanometer 1 is in the standby state in first step S50 of FIG. 12. In the standby state, for example, when the mode switch 13C is kept pressed for at least 3 seconds by the personnel of the hospital (step S51), the CPU 40 reads the latest air leakage level stored in the memory 41 and determines whether the air leakage level thus read is L1, L2, or L3 (step S52). Subsequently, as shown in steps S53 to S55, processing the same as the processing in steps S43 to S45 in the example in FIG. 11 is performed, and then the transition to the setting mode is made (step S56). Thereby, the CPU 40 stops the displaying the air leakage testing result in the first display mode (FIG. 14 or 17A). Therefore, it is guaranteed that the displaying the air leakage testing result in the first display mode is only temporarily provided.

As described above, this example can also provide the same effects that the example in FIG. 11 provides.

In the setting mode (step S56), a setting guide display (not illustrated) for facilitating various settings is made on the display device 11. In accordance with the setting guide display, the personnel of the hospital (specifically, maintenance personnel) can make various settings of the sphygmomanometer 1. The general patient usually would not see the sphygmomanometer 1 in the setting mode.

Figure 13:
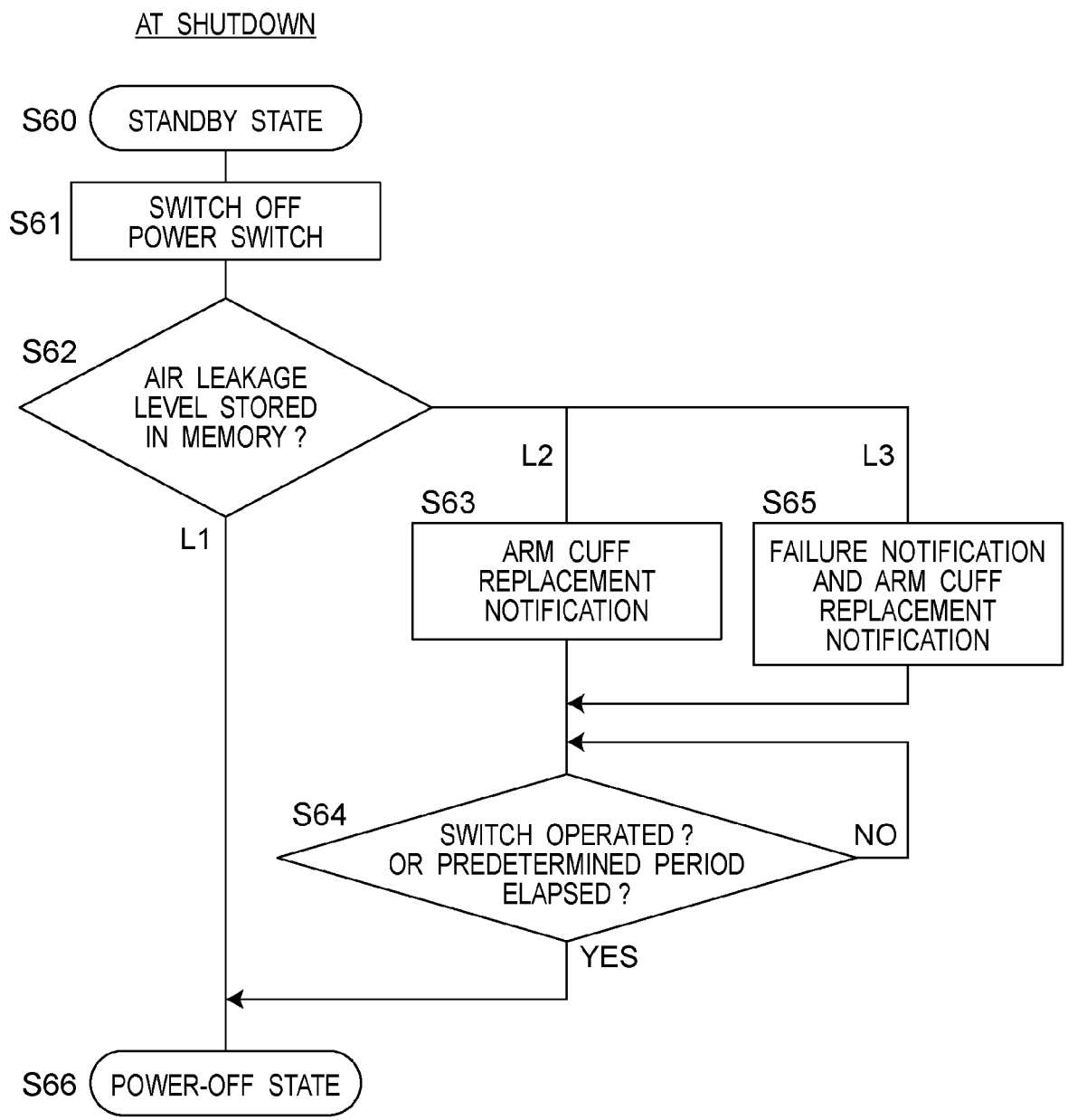
FIG. 13 is a diagram illustrating a flow of notification control during a transition from the standby state to the power-off state in (at the shutdown of) the sphygmomanometer.

(5) Notification Control During Transition from Standby State to Power-Off State FIG. 13 illustrates a flow of notification control during the transition from the standby state to the power-off state in (at the shutdown of) the sphygmomanometer 1.

In this example, it is assumed that the sphygmomanometer 1 is in the standby state in the first step S60 in FIG. 13, as in step S40 in FIG. 11. In this standby state, for example, when the power switch 10 is switched off by the personnel of the hospital (step S61), the CPU 40 reads the latest air leakage level stored in the memory 41 and determines whether the air leakage level thus read is L1, L2, or L3 (step S62). Subsequently, as shown in steps S63 to S65, processing the same as the processing in steps S43 to S45 in the example in FIG. 11 (or steps S53 to S55 in the example in FIG. 12) is performed, and then the transition to the power-off state is made (step S66). Thereby, the CPU 40 stops the displaying the air leakage testing result in the first display mode (FIG. 14 or 17A). Therefore, it is guaranteed that the displaying the air leakage testing result in the first display mode is only temporarily provided.

As described above, this example can also provide the same effects that the example in FIG. 11 (or the example in FIG. 12) provides.

Modification of Main Control

Figure 19:
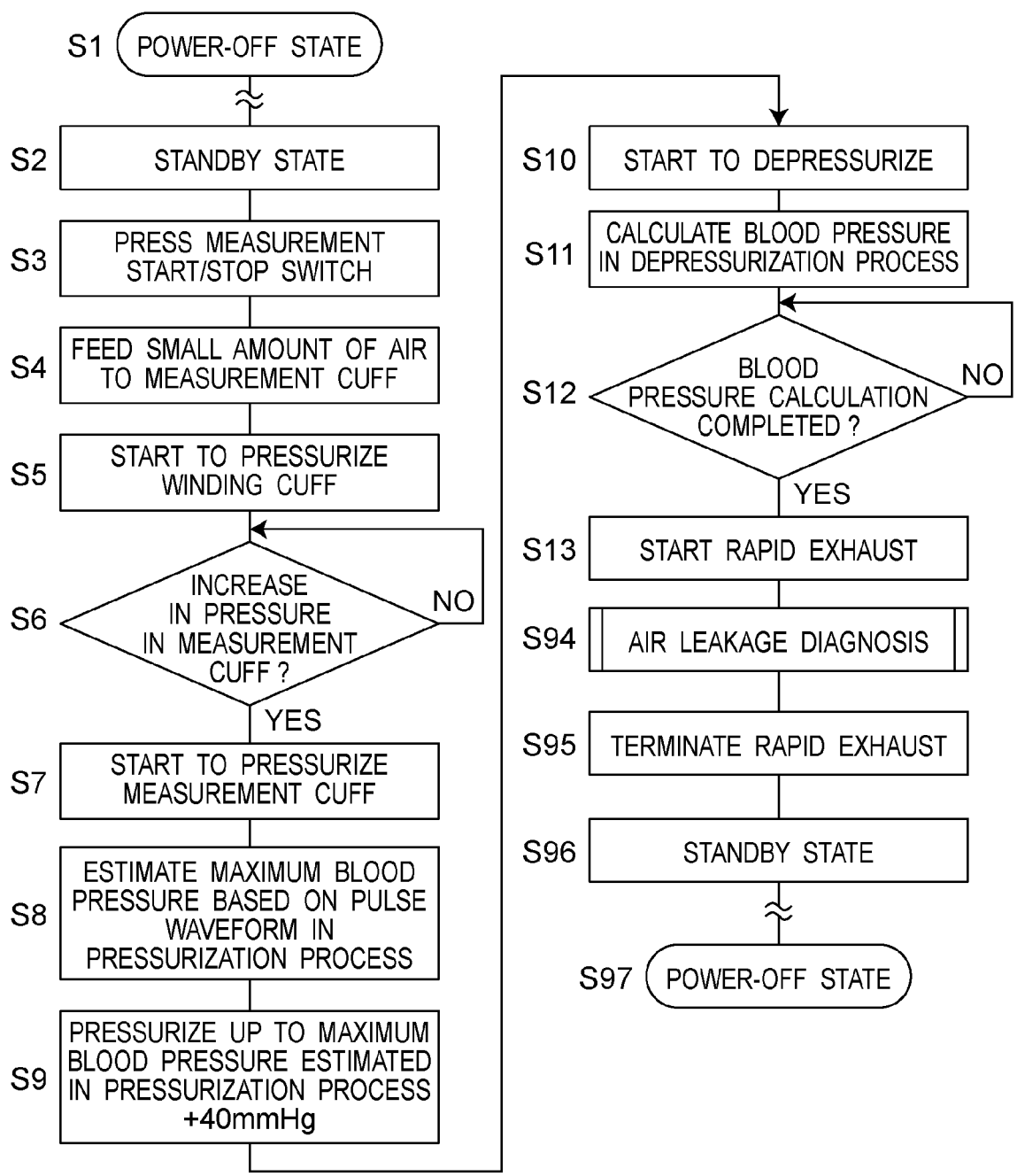
FIG. 19 is a diagram illustrating a flow of a modification of the main control in the sphygmomanometer.

FIG. 19 illustrates a flow of a modification of the above-described main control (FIG. 4). In the flow of this modification, processing proceeds from steps S1 to S13 in the same manner as in the flow of the above-described main control (in FIG. 19, the same steps as in FIG. 4 are denoted by the same reference numerals). Note that, in this example, at the start of the rapid exhaust in step S13, the CPU 40 makes displaying, on the display device 11, the blood pressure measurement result (the maximum blood pressure and the minimal blood pressure) and the pulse rate.

Figure 8:
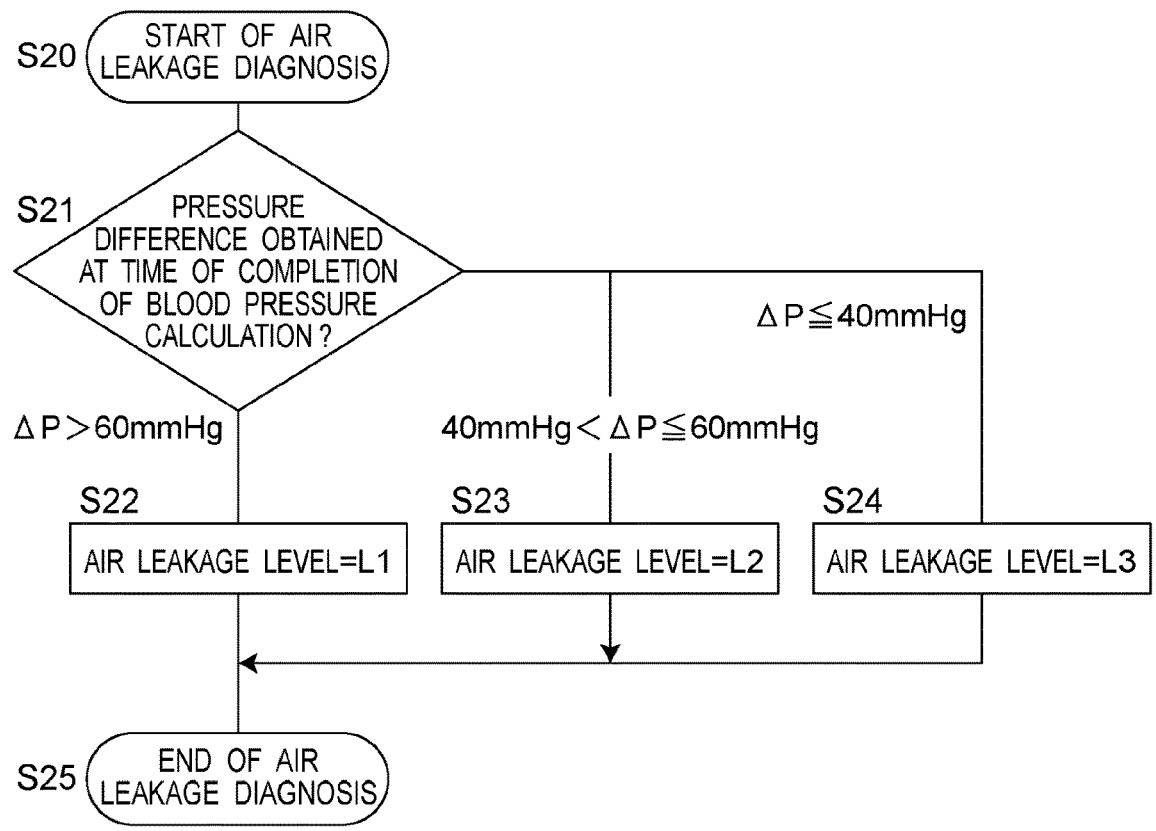
FIG. 8 is a diagram illustrating a flow of air leakage diagnosis processing in the sphygmomanometer.
Figure 20:
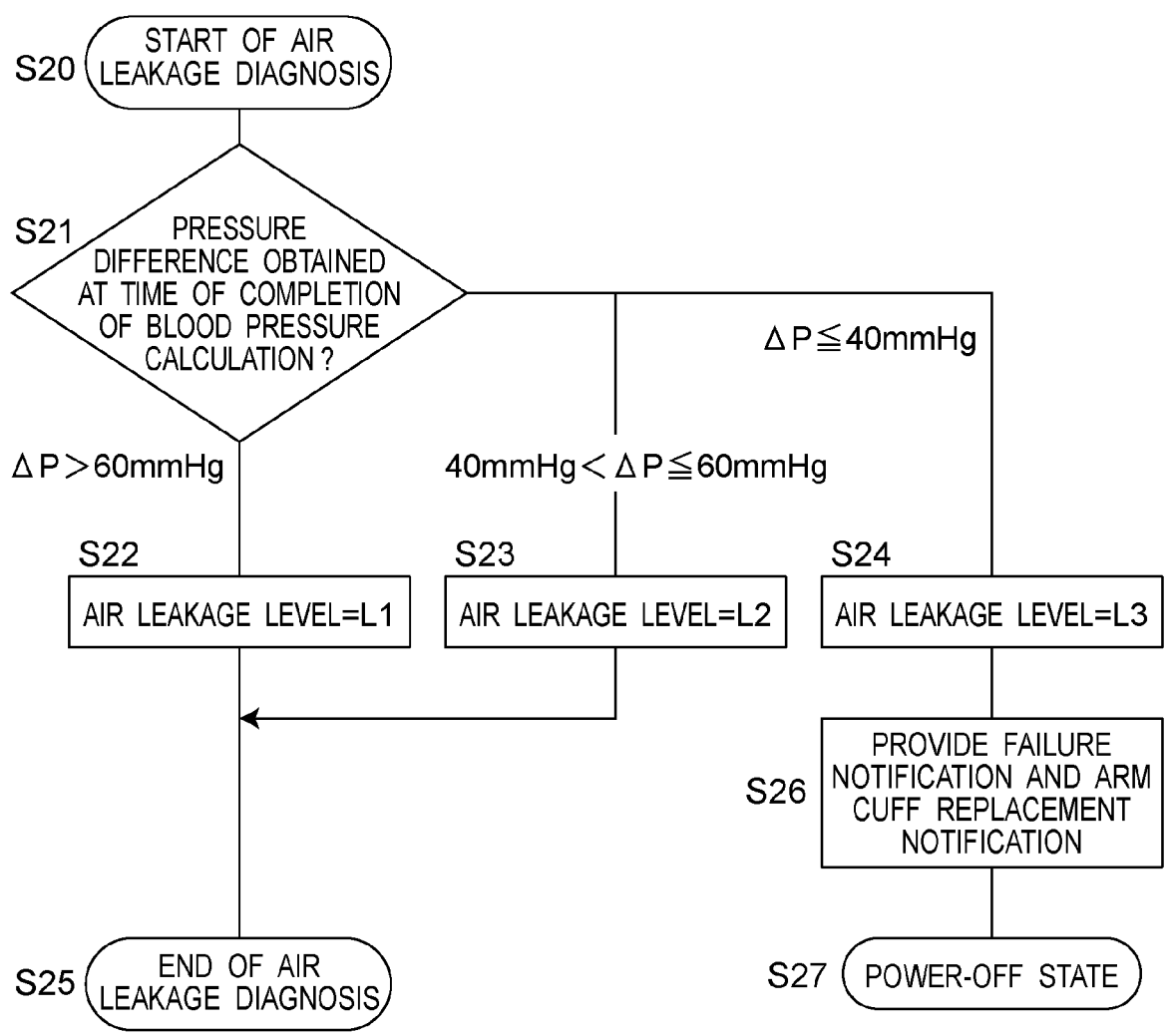
FIG. 20 is a diagram illustrating a detailed flow of air leakage diagnosis processing illustrated in FIG. 19.

Next, in step S94 in FIG. 19, the CPU 40 serves as an air leakage testing unit to perform air leakage diagnosis processing as shown in the flow in FIG. 20 instead of the above-described air leakage diagnosis processing (steps S20 to S25 in FIG. 8). In FIG. 20, the same steps as in FIG. 8 are denoted by the same reference numerals.

As in step S20 in FIG. 8, when the air leakage diagnosis is started in step S20 in FIG. 20, first, in step S21, the CPU 40 reads the latest pressure difference ΔP obtained at the time of completion of the blood pressure calculation and stored in the memory 41, and determines whether or not the pressure difference ΔP thus read is greater than 60 mmHg corresponding to the first reference value AL1, and whether or not the pressure difference ΔP thus read is greater than 40 mmHg corresponding to the second reference value AL2. When the pressure difference ΔP is greater than 60 mmHg (i.e. ΔP>60 mmHg), it is determined that the air leakage level of the air systems 20, 30 is the first air leakage level L1 (step S22). When the pressure difference ΔP is greater than 40 mmHg and equal to or less than 60 mmHg (i.e. 40 mmHg<ΔP≤60 mmHg), it is determined that the air leakage level of the air systems 20, 30 is the second air leakage level L2 (step S23). In either case, the CPU 40 stores the air leakage level L1 or L2 in the memory 41 and brings the air leakage diagnosis processing to an end (step S25). On the other hand, when the pressure difference ΔP is equal to or less than 40 mmHg (i.e. ΔP≤40 mmHg), it is determined that the air leakage level of the air systems 20, 30 is the third air leakage level L3 (step S24). In this case, the CPU 40 stores the air leakage level L3 in the memory 41 and serves as a notification control unit to make displaying, on the display device 11, an indication that the blood pressure measurement is disabled (failure notification and arm cuff replacement notification) immediately (that is, even at a timing when the general patient would see the sphygmomanometer 1) (step S26). The display indicating that the blood pressure measurement is disabled is the same as illustrated in FIG. 18A or 18B, for example. The personnel of the hospital can recognize, by viewing this display, that a failure has occurred and that the arm cuff (in this example, the cuff unit 5) needs to be replaced. Subsequently, the CPU 40 brings the sphygmomanometer 1 into the power-off state for safety (step S27).

When the air leakage diagnosis is brought to an end in step S25 in FIG. 20, the sphygmomanometer 1 is brought into the standby state after the rapid exhaust in step S95 in FIG. 19 (step S96). In this example, in this standby state, the same display as illustrated in FIG. 15 described above is made on the display device 11. This prevents the general patient from noticing the air leakage testing result. In this standby state, for example, when the power switch 10 is switched off by the personnel of the hospital, the sphygmomanometer 1 returns to the power-off state through the notification control (example illustrated in FIG. 13) during the above-described transition from the standby state to the power-off state (step S97).

As described above, according to the sphygmomanometer 1, the air leakage testing result is displayed on the display device 11 at a timing when the general patient would not see the sphygmomanometer 1. The personnel of the hospital can view the air leakage testing result displayed in the first display mode (FIG. 14 or 17A) on the display device 11 to easily recognize the air leakage testing result. At the timing when the general patient would see the sphygmomanometer 1, the air leakage testing result is not displayed, or, even when it is displayed, the air leakage testing result is displayed in the second display mode (FIG. 16 or 17C) lower in degree of enhancement. This generally prevents the general patient from noticing the air leakage testing result. As described above, in this sphygmomanometer 1, the notification control as described above allows the air leakage testing result to be notified, to the personnel of the hospital, in a mode that is difficult for the general patient to understand. As described above, in the sphygmomanometer 1, thanks to the notification control as described above, the air leakage testing result can be notified to the personnel of the hospital in a mode difficult for the general patient to understand.

When displaying the air leakage testing result in the first display mode (FIG. 14 or 17A) on the display device 11, the CPU 40 may provide notification of the air leakage testing result through not only the displaying but also means other than the display such as a buzzer sound or a voice. This allows the air leakage testing result to be thoroughly notified to the personnel of the hospital.

Further, according to the above-described embodiment, the cuff unit 5 includes the winding cuff 79, the curler 78, and the measurement cuff 77 in the outer peripheral member 70, but the present invention is not limited to the embodiment. A configuration where neither the winding cuff 79 nor the curler 78 is provided, and the measurement cuff 77 solely compresses the to-be-measured part may be employed. In such a configuration, instead of obtaining the air leakage testing result based on the pressure difference ΔP between the pressure Pt in the winding cuff 79 and the pressure Pc in the measurement cuff 77, the air leakage testing result can be obtained by observing the pressure in (that is, the amount of air leakage from) the measurement cuff 77 for a predetermined period. Then, the notification control as described above may be performed in accordance with the air leakage level indicated by the air leakage testing result.

Further, according to the above-described embodiment, each time the blood pressure measurement is performed, the sphygmomanometer 1 performs the air leakage testing, but the present invention is not limited to the embodiment. Every time a predetermined number of the blood pressure measurements are performed, the air leakage testing may be performed. Alternatively, regardless of the number of the blood pressure measurements, the air leakage testing may be periodically performed according to the lapse of time.

Further, according to the above-described embodiment, the sphygmomanometer 1 is installed in a hospital, but the present invention is not limited to the embodiment. The sphygmomanometer 1 may be installed in another medical institution such as a health center, or a healthcare room of a school or company.

As described above, a sphygmomanometer according to the present disclosure is a sphygmomanometer provided with an air system for use in blood pressure measurement and capable of performing air leakage testing on the air system, the sphygmomanometer comprising:

a main control unit configured to perform main control to make a transition from a power-off state to a standby state in response to a power-on operation, to perform blood pressure measurement using the air system in response to a measurement start operation in the standby state and make a transition to the standby state after the blood pressure measurement, and to make a transition to the power-off state in response to a power-off operation in the standby state;

an air leakage testing unit configured to perform air leakage testing on the air system to obtain an air leakage testing result of the air leakage testing;

a storage unit configured to store the air leakage testing result; and a notification control unit configured to perform notification control to make displaying, on a display device, the air leakage testing result stored in the storage unit in a first display mode during the transition from the power-off state to the standby state or a transition from the power-off state to a non-blood pressure measurement state where the measurement start operation is disabled, or during the transition from the standby state to the power-off state or a transition from the standby state to the non-blood pressure measurement state where the measurement start operation is disabled, and not to make displaying the air leakage testing result or to make displaying the air leakage testing result in a second display mode lower in degree of enhancement than the first display mode in the standby state or during the blood pressure measurement.

Herein, a "power-off state" refers to a state where power is not supplied to the sphygmomanometer.

A "power-on operation" refers to an operation of powering on the sphygmomanometer by, for example, personnel of a medical institution such as an operation of switching on a power switch provided on the sphygmomanometer or an operation of connecting a power cable connected to the sphygmomanometer to a power outlet. Conversely, a "power-off operation" refers to an operation of powering off the sphygmomanometer by, for example, the personnel of the medical institution such as operation of switching off the power switch provided on the sphygmomanometer or an operation of removing the power cable connected to the sphygmomanometer from a power outlet. The "power-on operation" and the "power-off operation" may be each, for example, a remote operation using radio communication.

A "measurement start operation" refers to an operation of pressing a measurement start switch provided on the sphygmomanometer by, for example, a subject (typically, a patient). Further, for example, when the sphygmomanometer includes a tubular cuff and a sensor that detects insertion of an arm into the cuff and is configured to start to perform blood pressure measurement in accordance with an output of the sensor (indicating that the arm is inserted into the cuff), the "measurement start operation" may correspond to an operation of inserting his/her arm into the cuff by the subject.

A "standby state" refers to a state of waiting for the measurement start operation, that is, a state of being ready to perform blood pressure measurement in response to the measurement start operation. The standby state allows a display device to provide a display (for example, a display indicating that power is being supplied). With the sphygmomanometer installed in a medical institution such as a hospital, a general patient usually would see the sphygmomanometer only when the sphygmomanometer is in the standby state or is in operation for the blood pressure measurement.

A "non-blood pressure measurement state where the measurement start operation is disabled" refers to a non-blood pressure measurement state similar to the standby state but different from the standby state in that the measurement start operation is disabled. Examples of the "non-blood pressure measurement state where the measurement start operation is disabled" include a state where the sphygmomanometer is under maintenance (maintenance mode), and a state where various settings that define the operation of the sphygmomanometer are made (setting mode).

A "first display mode" for the displaying the air leakage testing result is defined as a mode where, for example, a person viewing the display can easily recognize the air leakage testing result. A "second display mode" is a mode lower in degree of enhancement than the first display mode, that is, an inconspicuous mode.

In the sphygmomanometer according to the present disclosure, the main control unit performs main control to make a transition to the standby state in response to the power-on operation, perform the blood pressure measurement using the air system in response to the measurement start operation in the standby state and make a transition to the standby state after the blood pressure measurement, and make a transition to the power-off state in response to the power-off operation in the standby state. The air leakage testing unit performs the air leakage testing on the air system in conjunction with, for example, the blood pressure measurement to obtain an air leakage testing result of the air leakage testing. The storage unit stores the air leakage testing result. The notification control unit makes displaying, on the display device, the air leakage testing result stored in the storage unit in the first display mode during the transition from the power-off state to the standby state or the non-blood pressure measurement state where the measurement start operation is disabled, or during the transition from the standby state to the power off state or the non-blood pressure measurement state where the measurement start operation is disabled. That is, in a case where the sphygmomanometer is installed in a medical institution such as a hospital, the air leakage testing result is displayed on the display device at a timing when a general patient would not see the sphygmomanometer. Personnel of the medical institution (receptionist, maintenance personnel (medical engineer), doctor, nurse, or the like) can easily recognize the air leakage testing result by viewing the air leakage testing result displayed on the display device in the first display mode. On the other hand, the notification control unit does not display the air leakage testing result or makes displaying the air leakage testing result in the second display mode lower in degree of enhancement than the first display mode in the standby state or during the blood pressure measurement. That is, in a case where the sphygmomanometer is installed in a medical institution such as a hospital, at the timing when the general patient would see the sphygmomanometer, the air leakage testing result is not displayed, or, even when it is displayed, the air leakage testing result is displayed in the second display mode. This generally prevents the general patient from noticing the air leakage testing result. Accordingly, by the sphygmomanometer, thanks to the notification control by the notification control unit, the air leakage testing result can be notified to personnel of a medical institution in a mode difficult for the general patient to understand.

When displaying the air leakage testing result in the first display mode on the display device, the notification control unit may provide notification of the air leakage testing result through not only the displaying but also means other than the displaying such as a buzzer sound or a voice. This allows the air leakage testing result to be thoroughly notified to the personnel of the medical institution.

In the sphygmomanometer of one embodiment, when a display stop operation is performed or a predetermined period elapses after having started to make displaying the air leakage testing result, the notification control unit makes the transition from the power-off state to the standby state or the non-blood pressure measurement state where the measurement start operation is disabled or the transition from the standby state to the power-off state or the non-blood pressure measurement state where the measurement start operation is disabled, and stops the displaying the air leakage testing result in the first display mode.

Here, the "display stop operation" refers to an operation of inputting, by, for example, the personnel of the medical institution, an instruction to stop the displaying the air leakage testing result in the first display mode. The "display stop operation" typically refers to an operation of pressing a display stop switch for inputting the instruction to stop the displaying the air leakage testing result in the first display mode. Further, the "display stop operation" may be, for example, a remote operation using radio communication.

In the sphygmomanometer according to this embodiment, when a display stop operation is performed or a predetermined period elapses after having started to make displaying the air leakage testing result, the notification control unit makes the transition from the power-off state to the standby state or the non-blood pressure measurement state where the measurement start operation is disabled or the transition from the standby state to the power-off state or the non-blood pressure measurement state where the measurement start operation is disabled, and stops the displaying the air leakage testing result in the first display mode. Therefore, it is guaranteed that the displaying the air leakage testing result in the first display mode is only temporarily provided. For example, even when the personnel of the medical institution forgets to press the display stop switch after the displaying the air leakage testing result in the first display mode has been started, it is possible to prevent the general patient from noticing the air leakage testing result. Note that after the displaying in the first display mode has been stopped, the notification control unit may make displaying in the second display mode which is lower in degree of enhancement than the first display mode.

In the sphygmomanometer of one embodiment,
the air leakage testing result includes at least three air leakage levels of a first air leakage level indicating that an air leakage amount of the air system is smaller than a predetermined first reference value, a third air leakage level indicating that the air leakage amount of the air system is larger than a second reference value set greater than the first reference value, and a second air leakage level indicating that the air leakage amount of the air system corresponds to a value between the first reference value and the second reference value, and
the notification control unit performs the notification control only when the air leakage testing result is the second air leakage level among the three air leakage levels, does not display the air leakage testing result when the air leakage testing result is the first air leakage level, and makes displaying, on the display device, an indication that the blood pressure measurement is disabled when the air leakage testing result is the third air leakage level.

Here, the "first air leakage level" typically corresponds to a normal level including a case where there is no air leakage. The "third air leakage level" typically corresponds to a failure level, that is, a level at which the blood pressure measurement can no longer be performed by the sphygmomanometer. The "second air leakage level" corresponds to a level between the first air leakage level and the third air leakage level. Generally speaking, for example, when the sphygmomanometer is repeatedly used, the air leakage amount of the air system tends to gradually increase. Therefore, the "second air leakage level" corresponds to an initial stage where air has just started to leak from the air system.

In the sphygmomanometer according to this embodiment, the air leakage testing result includes at least three air leakage levels of the first air leakage level, the third air leakage level, and the second air leakage level corresponding to a level between the first air leakage level and the third air leakage level. The notification control unit performs the notification control only when the air leakage testing result is the second air leakage level among the three air leakage levels, does not display the air leakage testing result when the air leakage testing result is the first air leakage level, and makes displaying, on the display device, an indication that the blood pressure measurement is disabled when the air leakage testing result is the third air leakage level. For example, when the air leakage testing result is the second air leakage level, and the air leakage testing result is displayed on the display device in the first display mode in response to the second air leakage level, the personnel of the medical institution notices that it is an initial stage where air has just started to leak from the air system. This allows the personnel of the medical institution (particularly, maintenance personnel) to replace a component of the air system or prepare a component for replacement. This in turn makes it possible to prevent a failure from occurring, or, even when a failure occurs, this makes it possible to shorten, by immediately replacing a corresponding component with a new component, a time during which the blood pressure measurement is disabled. Further, the notification control unit makes displaying, on the display device, an indication that the blood pressure measurement is disabled when the air leakage testing result is the third air leakage level. This prevents the general patient from pressing the measurement start switch in vain to perform the blood pressure measurement.

In the sphygmomanometer of one embodiment,
the air leakage testing unit performs the air leakage testing on the air system in conjunction with the blood pressure measurement, and
each time the air leakage testing is performed on the air system, the storage unit stores the air leakage testing result of the air leakage testing.

In the sphygmomanometer according to this embodiment, the air leakage testing unit performs the air leakage testing on the air system in conjunction with the blood pressure measurement. Therefore, even when the user does not input an instruction to start the air leakage testing, the air leakage testing can be automatically performed. Further, each time the air leakage testing is performed on the air system, the storage unit stores the air leakage testing result of the air leakage testing. Therefore, the storage unit stores the latest air leakage testing result. This allows the notification control unit to display the latest air leakage testing result.

The sphygmomanometer of one embodiment, further comprises a cuff unit having a cylindrical shape for an upper arm to be inserted, wherein
the cuff unit includes an outer peripheral member having a cylindrical shape, a winding air bag annularly disposed along an inner circumferential surface of the outer peripheral member, a curler formed of a flexible plate material curved and disposed along an inner circumferential surface of the winding air bag, the curler being reduced in diameter when the winding air bag is pressurized to expand radially inward, and a measurement air bag disposed along an inner circumferential surface of the curler, the measurement air bag being pressurized for the blood pressure measurement to compress the upper arm, and
the air leakage testing unit obtains the air leakage testing result based on a pressure difference between a pressure in the winding air bag and a pressure in the measurement air bag at a time when a blood pressure calculation is completed in a depressurization process for the blood pressure measurement.

Here, the "a time when a blood pressure calculation is completed" refers to a time immediately before the winding air bag and the measurement air bag are rapidly exhausted after the blood pressure calculation based on the pressure in the measurement air bag is completed. Specifically, the winding cuff and the measurement cuff are pressurized and subsequently depressurized during the blood pressure measurement, but a certain degree of pressure remains in the winding cuff and the measurement cuff until the blood pressure calculation is completed. After the blood pressure calculation is completed, the winding cuff and the measurement cuff are rapidly exhausted to release the pressure. The "a time when a blood pressure calculation is completed" refers to a time immediately before the rapid exhaust.

For a type of sphygmomanometer including the above-described cuff unit, the inventors have empirically obtained findings that most of the failure cases are caused by air leakage from the winding cuff.

Therefore, in the sphygmomanometer according to this embodiment, the air leakage testing unit obtains the air leakage testing result based on the pressure difference between a pressure in the winding cuff and a pressure in the measurement cuff at a time when a blood pressure calculation is completed in a depressurization process for the blood pressure measurement. This allows air leakage from the winding cuff to be detected with high accuracy based on the pressure in the measurement cuff.

In the sphygmomanometer of one embodiment,
the displaying the air leakage testing result in the first display mode is made as a display of a message indicating a measure against the air leakage testing result, and
the displaying the air leakage testing result in the second display mode is made as a display of an icon corresponding to the air leakage testing result.

In the sphygmomanometer according to this embodiment, since the displaying the air leakage testing result in the first display mode is made as a display of the message indicating a measure against the air leakage testing result, the personnel of the medical institution can easily recognize the air leakage testing result by viewing the message and take a measure indicated by the message. On the other hand, since the displaying the air leakage testing result in the second display mode is made as a display of the icon corresponding to the air leakage testing result, the displaying the air leakage testing result in the second display mode is lower in degree of enhancement than the above-described message. The general patient who does not know the meaning of the icon would not notice that the air leakage testing result is displayed. The personnel of the medical institution (particularly, maintenance personnel) who knows the meaning of the icon can recognize the air leakage testing result by viewing the icon and take a measure suggested by the icon.

In the sphygmomanometer of one embodiment,
the displaying the air leakage testing result in the first display mode is made as a display where an icon corresponding to the air leakage testing result blinks, and
the displaying the air leakage testing result in the second display mode is made as a display where the icon is kept lit.

In the sphygmomanometer according to this embodiment, since the displaying the air leakage testing result in the first display mode is made as a display where an icon corresponding to the air leakage testing result blinks, it is conspicuous. This allows the personnel of the medical institution who knows the meaning of the icon to easily recognize the air leakage testing result by viewing the icon and take a measure suggested by the icon. On the other hand, since the displaying the air leakage testing result in the second display mode is made as a display where the icon is kept lit, the displaying the air leakage testing result in the second display mode is inconspicuous as compared with the displaying in a blinking manner. Therefore, the general patient who does not know the meaning of the icon would not notice that the air leakage testing result is displayed.

As is apparent from the above, the sphygmomanometer according to the present disclosure can notify personnel of a medical institution of the air leakage testing result in a mode difficult for a general patient to understand the air leakage testing result.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:
1. A sphygmomanometer provided with an air system for blood pressure measurement and capable of performing air leakage testing on the air system, the air system comprising at least a cuff configured to surround a to-be-measured part, a pump connected to the cuff via a first fluid pipe, and a valve connected to the cuff via a second fluid pipe, the sphygmomanometer comprising:
a processor;
a memory; and
a display, wherein
the processor is configured to act as:
a main control unit to perform main control to make a first transition from a power-off state to a standby state in response to a power-on operation, to perform blood pressure measurement by driving the pump to feed an air to the cuff through the first fluid pipe to pressurize the cuff or driving the valve to exhaust the air from the cuff through the second fluid pipe to depressurize the cuff in response to a measurement start operation in the standby state, to make a second transition to the standby state after the blood pressure measurement, and to make a third transition to the power-off state in response to a power-off operation in the standby state;
an air leakage testing unit to perform, after the blood pressure measurement and before the second transition, air leakage testing on the air system to obtain an air leakage testing result of the air leakage testing, and to cause the memory to store the air leakage testing result; and
a notification control unit to perform notification control to control display contents on the display based on the air leakage testing result stored in the memory, wherein
the air leakage testing result includes at least three air leakage levels of a first air leakage level as an acceptable level indicating that an air leakage amount of the air system is smaller than a predetermined first reference value, a third air leakage level as a failure level indicating that the air leakage amount of the air system is larger than a second reference value set greater than the first reference value, and a second air leakage level indicating that the air leakage amount of the air system corresponds to a value between the first reference value and the second reference value,
the processor acting as the notification control unit is configured:
when the air leakage testing result is the second air leakage level,
to display, during the first transition, on the display, the air leakage testing result in a first display mode displaying a message to notify a replacement of the cuff or displaying a first icon corresponding to the air leakage testing result with blinking,
to display, in the standby state, on the display, that the blood pressure measurement is enabled without displaying the air leakage testing result or with displaying the air leakage testing result in a second display mode,
to not display the air leakage testing result during the blood pressure measurement and the second transition, and
to display, on the display, the air leakage testing result in a first display mode during the third transition, wherein
when the displaying of the air leakage testing result in the first display mode is displaying the message, the displaying of the air leakage testing result in the second display mode is displaying a second icon corresponding to the air leakage testing result, and when the displaying of the air leakage testing result in the first display mode is displaying the first icon with blinking, the displaying of the air leakage testing result in the second display mode is displaying the first icon with being kept lit.

2. The sphygmomanometer according to claim 1, wherein when the air leakage testing result is the second air leakage level, the processor acting as the notification control unit is configured, during the first or third transition, to stop the displaying of the air leakage testing result in the first display mode, when a display stop operation is performed or a predetermined period elapses after having started displaying the air leakage testing result in the first display mode.

3. The sphygmomanometer according to claim 1, wherein the processor acting as the notification control unit is configured:
to not display the air leakage testing result, during the first, second and third transitions, when the air leakage testing result is the first air leakage level, and
to display, on the display, an indication that the blood pressure measurement is disabled, during the first, second and third transitions, when the air leakage testing result is the third air leakage level.

4. The sphygmomanometer according to claim 1, wherein the processor acting as the air leakage testing unit causes, each time the air leakage testing is performed on the air system, the memory to store the air leakage testing result of the air leakage testing.

5. The sphygmomanometer according to claim 1, wherein the cuff comprises a cuff unit having a cylindrical shape, the cuff unit includes an outer peripheral member having a cylindrical shape, a winding air bag annularly disposed along an inner circumferential surface of the outer peripheral member, a curler formed of a flexible plate material curved and disposed along an inner circumferential surface of the winding air bag, the curler being reduced in diameter when the winding air bag is pressurized to expand radially inward, and a measurement air bag disposed along an inner circumferential surface of the curler and configured to be pressurized for the blood pressure measurement to compress an upper arm as the to-be-measured part, and
the processor acting as the air leakage testing unit obtains the air leakage testing result based on a pressure difference between a pressure in the winding air bag and a pressure in the measurement air bag at a time when a blood pressure calculation is completed in a depressurization process for the blood pressure measurement.

6. The sphygmomanometer according to claim 1, wherein the processor acting as the main control unit is further configured to perform to make, in response to a maintenance mode transition operation, a fourth transition from the power-off state to a maintenance mode where the measurement start operation is disabled and a maintenance of the sphygmomanometer is to be performed, and to make, in response to a setting mode transition operation, a fifth transition from the standby state to a setting mode where the measurement start operation is disabled and a setting for the sphygmomanometer is to be performed,
the processor acting as the notification control unit is configured:
to not display the air leakage testing result, during the fourth and fifth transitions, when the air leakage testing result is the first air leakage level,
to display, on the display, the air leakage testing result in the first display mode, during the fourth and fifth transitions, when the air leakage testing result is the second air leakage level, and
to display, on the display, an indication that the blood pressure measurement is disabled, during the fourth and fifth transitions, when the air leakage testing result is the third air leakage level.

* * * * *